(12) United States Patent
Kagawa et al.

(10) Patent No.: US 10,051,193 B2
(45) Date of Patent: Aug. 14, 2018

(54) PROCESSING DEVICE, IMAGING DEVICE, AND ENDOSCOPE SYSTEM

(71) Applicant: OLYMPUS CORPORATION, Tokyo (JP)

(72) Inventors: Ryohei Kagawa, Hachioji (JP); Kotaro Ogasawara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/351,527

(22) Filed: Nov. 15, 2016

(65) Prior Publication Data

US 2017/0064178 A1 Mar. 2, 2017

Related U.S. Application Data

(63) Continuation of application No. PCT/JP2015/066557, filed on Jun. 9, 2015.

(30) Foreign Application Priority Data

Jun. 18, 2014 (JP) ................................ 2014-125360

(51) Int. Cl.
*A61B 1/04* (2006.01)
*A61B 1/05* (2006.01)
(Continued)

(52) U.S. Cl.
CPC ....... *H04N 5/2353* (2013.01); *A61B 1/00009* (2013.01); *A61B 1/00045* (2013.01);
(Continued)

(58) Field of Classification Search
None
See application file for complete search history.

(56) References Cited

U.S. PATENT DOCUMENTS 8,767,095 B2 7/2014 Fukushima
9,137,453 B2 9/2015 Tanaka et al.
(Continued)

FOREIGN PATENT DOCUMENTS

EP 1 420 592 A1 5/2004
JP 2000-300514 A 10/2000
(Continued)

OTHER PUBLICATIONS

International Search Report dated Sep. 1, 2015 issued in PCT/JP2015/066557.
(Continued)

*Primary Examiner* — Kevin McInnish
(74) *Attorney, Agent, or Firm* — Scully, Scott, Murphy & Presser, P.C.

(57) ABSTRACT

A processing device includes a signal processing unit configured to: input first and second pixel signals from an image sensor having pixels for receiving light from a subject illuminated with pulsed light and generating a pixel signal, the first pixel signal being a one-frame signal read at read timing at least a part of which is included in an illumination period of the pulsed light, the second pixel signal being a one-frame signal read after the one frame of the first pixel signal; and generate a one-frame third pixel signal by synthesizing first and second overlap pixel signals, the first overlap pixel signal being defined as the first pixel signal corresponding to an overlap line of the pixels in which the illumination period of the pulsed light is overlapped with the read timing, the second overlap pixel signal being defined as the second pixel signal corresponding to the overlap line.

19 Claims, 18 Drawing Sheets

(51) Int. Cl.
*H04N 5/235* (2006.01)
*G03B 7/093* (2006.01)
*H04N 5/225* (2006.01)
*H04N 5/243* (2006.01)
*A61B 1/00* (2006.01)
*G02B 23/24* (2006.01)
*H04N 5/372* (2011.01)
*H04N 5/374* (2011.01)
*H04N 5/378* (2011.01)

(52) U.S. Cl.
CPC ............ *A61B 1/00096* (2013.01); *A61B 1/04* (2013.01); *A61B 1/05* (2013.01); *G02B 23/2446* (2013.01); *G02B 23/2469* (2013.01); *G02B 23/2484* (2013.01); *G03B 7/093* (2013.01); *H04N 5/225* (2013.01); *H04N 5/2256* (2013.01); *H04N 5/243* (2013.01); *H04N 5/372* (2013.01); *H04N 5/374* (2013.01); *H04N 5/378* (2013.01); *H04N 2005/2255* (2013.01)

(56) References Cited

U.S. PATENT DOCUMENTS

2003/0001951 A1* 1/2003 Tsujita ................... A61B 1/043
                                                          348/65
2004/0095464 A1* 5/2004 Miyagi ................ A61B 1/2673
                                                          348/65
2008/0232130 A1   9/2008 Suda
2009/0147077 A1   6/2009 Tani et al.
2013/0300849 A1* 11/2013 Ono ................... A61B 1/00006
                                                          348/68
2014/0198249 A1   7/2014 Tanaka et al.

FOREIGN PATENT DOCUMENTS

| JP | 2008-229222 A | 10/2008 |
| JP | 2009-136447 A | 6/2009 |
| JP | 2010-135921 A | 6/2010 |
| JP | 2011-259406 A | 12/2011 |
| JP | 2012-019429 A | 1/2012 |
| WO | WO 2013/099942 A1 | 7/2013 |
| WO | 2014/017165 A1 | 1/2014 |

OTHER PUBLICATIONS

Japanese Office Action dated Mar. 7, 2016 issued in Japanese Patent Application No. 2015-560449.

Extended Supplementary European Search Report dated Jan. 25, 2018 in European Patent Application No. 15 80 9065.4.

* cited by examiner

PROCESSING DEVICE, IMAGING DEVICE, AND ENDOSCOPE SYSTEM

CROSS REFERENCES TO RELATED APPLICATIONS

This application is a continuation of PCT international application Ser. No. PCT/JP2015/066557, filed on Jun. 9, 2015 which designates the United States, incorporated herein by reference, and which claims the benefit of priority from Japanese Patent Application No. 2014-125360, filed on Jun. 18, 2014, incorporated herein by reference.

BACKGROUND

1. Technical Field

The disclosure relates to a processing device for processing a pixel signal, an imaging device, and an endoscope system.

2. Related Art

Conventionally, in the medical field, an endoscope system is used to observe the inside of a subject. In general, the endoscope system captures an in-vivo image by inserting a flexible insertion unit having an elongated shape into the subject such as a patient, intermittently emitting illumination light from the distal end of the insertion unit, and receiving reflected light of the illumination light by using an imaging unit at a distal end portion of the insertion unit. The in-vivo image captured in this way is displayed on a display of the endoscope system.

When imaging is performed under intermittent illumination, a variation in brightness occurs between images depending on an exposure timing of an image sensor, so that the images may flick when the images are displayed on the display. In particular, when employing a CMOS (Complementary Metal Oxide Semiconductor) image sensor and applying a rolling shutter method that changes timing of exposure and reading for each horizontal line, an exposure timing varies for each horizontal line in one imaging period, so that luminance unevenness easily occurs.

In order to address such a situation, conventionally, a technique is proposed that generates a display image by removing areas having luminance greater than or equal to a predetermined threshold value from a frame image (for example, see JP 2010-135921 A). In addition to the technique described in Patent Literature 1 that removes part of an image, a technique is also proposed that can secure a certain level of luminance in the entire area of an image by causing a light source to emit illumination light in a period common to all pixels in an exposure period of each pixel of an image sensor (for example, see JP 2009-136447 A).

SUMMARY

In some embodiments, a processing device includes a signal processing unit configured to: input first and second pixel signals from an image sensor having a plurality of pixels that is configured to receive light from a subject illuminated with pulsed light and to generate a pixel signal, the first pixel signal being a pixel signal of one frame that is read at read timing at least a part of which is included in an illumination period of the pulsed light, the second pixel signal being a pixel signal of one frame that is read at read timing of one frame after the first pixel signal; and generate a third pixel signal of one frame by synthesizing first and second overlap pixel signals, the first overlap pixel signal being defined as the first pixel signal corresponding to an overlap line of the plurality of pixels in which the illumination period of the pulsed light is overlapped with the read timing, the second overlap pixel signal being defined as the second pixel signal corresponding to the overlap line.

In some embodiments, an imaging device includes: a light receiving unit having a plurality of pixels that is configured to receive light from a subject illuminated with pulsed light and to generate a pixel signal; a reading unit configured to perform exposure on the plurality of pixels of the light receiving unit and to read the pixel signal from the plurality of pixels of the light receiving unit; and a signal processing unit configured to generate, from first and second pixel signals, a third pixel signal of one frame by synthesizing first and second overlap pixel signals, the first pixel signal being a pixel signal of one frame that is read by the reading unit at read timing at least a part of which is included in an illumination period of the pulsed light, the second pixel signal being a pixel signal of one frame that is read at read timing of one frame after the first pixel signal, the first overlap pixel signal being defined as the first pixel signal corresponding to an overlap line of the plurality of pixels in which the illumination period of the pulsed light is overlapped with the read timing, the second overlap pixel signal being defined as the second pixel signal corresponding to the overlap line.

In some embodiments, an endoscope system includes: a light source configured to emit pulsed light to illuminate a subject; a light receiving unit having a plurality of pixels configured to receive light from the subject illuminated with the pulsed light emitted from the light source and to generate a pixel signal; a reading unit configured to perform exposure on the plurality of pixels of the light receiving unit and to read the pixel signal from the plurality of pixels of the light receiving unit; and a signal processing unit configured to generate, from first and second pixel signals, a third pixel signal of one frame by synthesizing first and second overlap pixel signals, the first pixel signal being a pixel signal of one frame that is read by the reading unit at read timing at least a part of which is included in an illumination period of the pulsed light, the second pixel signal being a pixel signal of one frame that is read at read timing of one frame after the first pixel signal, the first overlap pixel signal being defined as the first pixel signal corresponding to an overlap line of the plurality of pixels in which the illumination period of the pulsed light is overlapped with the read timing, the second overlap pixel signal being defined as the second pixel signal corresponding to the overlap line.

The above and other features, advantages and technical and industrial significance of this invention will be better understood by reading the following detailed description of presently preferred embodiments of the invention, when considered in connection with the accompanying drawings.

DETAILED DESCRIPTION

Reference will be made below to an endoscope system as modes for carrying out the present invention (hereinafter referred to as "embodiment(s)"). The present invention is not limited by the embodiments. The same reference signs are used to designate the same elements throughout the drawings. The drawings are schematic, and it is noted that the relation between the thickness and the width of each member and the ratio of the size of each member are different from the reality. The size and the ratio of the same element may be different in a different drawing.

First Embodiment

Figure 1:
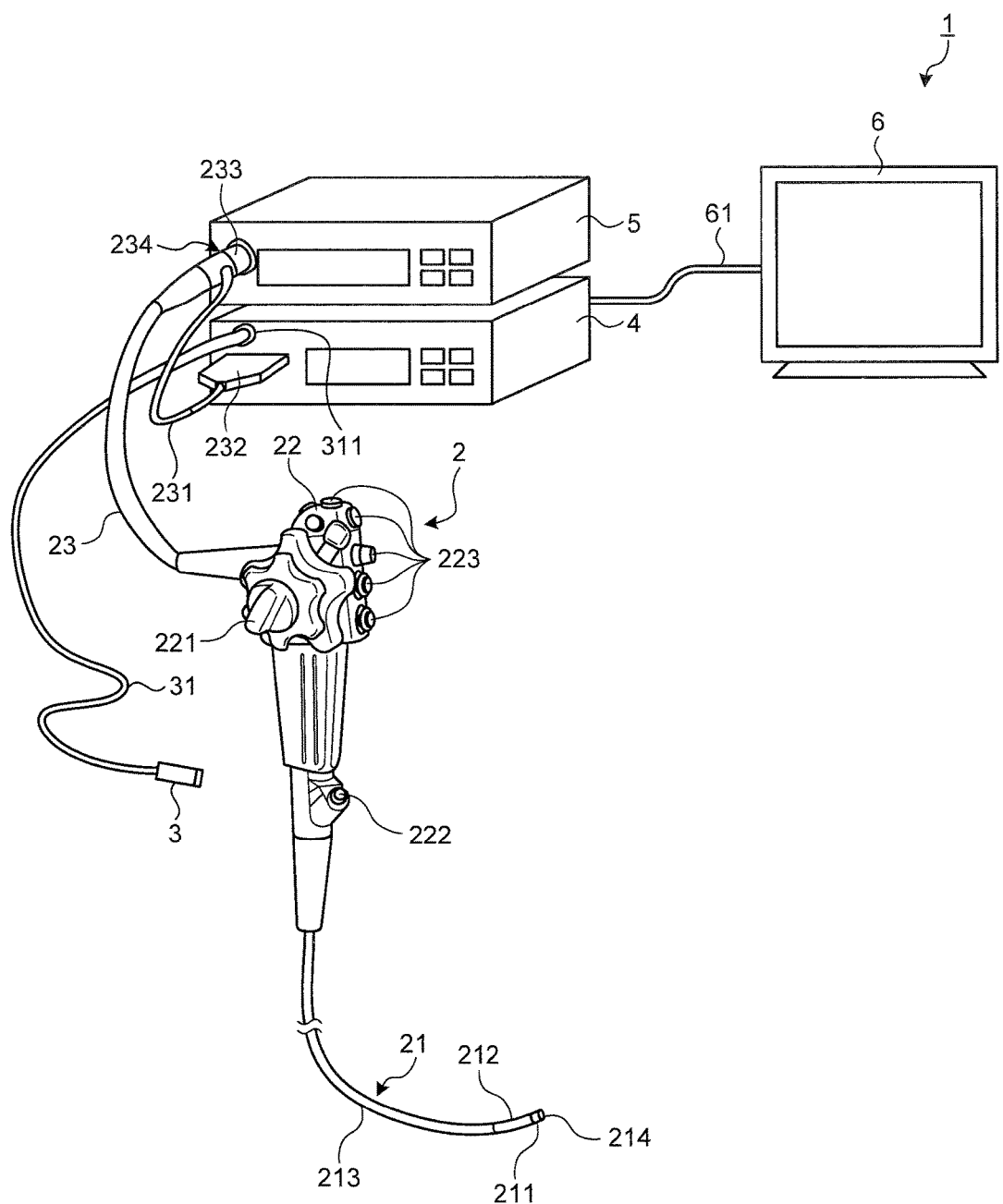
FIG. 1 is a schematic diagram illustrating a schematic configuration of an endoscope system according to a first embodiment of the present invention.

FIG. 1 is a schematic diagram illustrating a schematic configuration of an endoscope system according to a first embodiment of the present invention. As illustrated in FIG. 1, the endoscope system 1 according to the first embodiment includes an endoscope 2 (scope) which is introduced into a subject and captures an image inside the subject to generate an image signal of inside of the subject, a voice input device 3 to which a voice is input, a light source device 5 that generates pulsed light as illumination light (observation light) of the endoscope 2, a processing device 4 which performs predetermined image processing on the image signal captured by the endoscope 2 and controls each element of the endoscope system 1, and a display device 6 which displays an image corresponding to the image signal on which the processing device 4 performs the image processing.

The endoscope 2 includes an insertion unit 21 that is inserted into the subject, an operating unit 22 which is provided at a proximal end portion of the insertion unit 21 and held by an operator, and a flexible universal cord 23 that extends from the operating unit 22.

The insertion unit 21 is realized by using an illumination fiber (light guide cable), an electric cable, and the like. The insertion unit 21 includes a distal end portion 211 including an imaging unit incorporating a CMOS image sensor as an image sensor that captures an image inside the subject, a bendable bending portion 212 formed by a plurality of bending pieces, and a flexible tube portion 213 having flexibility provided at the proximal end portion of the bending portion 212. The distal end portion 211 is provided with an illumination unit that illuminates inside the subject through an illumination lens, an observation unit that captures an image inside the subject, an opening portion 214 through which a processing tool channel passes, and an air/water nozzle (not illustrated in FIG. 1).

The operating unit 22 includes a bending knob 221 that bends the bending portion 212 in a vertical direction and a horizontal direction, a treatment tool insertion portion 222 through which treatment tools such as biopsy forceps and a laser scalpel are inserted into a body cavity of the subject, and a plurality of switch units 223 for operating peripheral apparatuses such as the processing device 4, the light source device 5, an air supply device, a water supply device, and a gas supply device. A treatment tool inserted from the treatment tool insertion portion 222 is exposed from the opening portion 214 at the distal end of the insertion unit 21 through a treatment tool channel provided inside the insertion unit 21.

The universal cord 23 is formed by using an illumination fiber, an electric cable, and the like. The universal cord 23 is split at its proximal end. An end portion of one branch cord 231 is a connector 232 and the proximal end of the other branch cord 234 is a connector 233. The connector 232 is attachable to and detachable from the processing device 4. The connector 233 is attachable to and detachable from the light source device 5. The universal cord 23 transmits an image signal captured by the imaging unit provided in the distal end portion 211 to the processing device 4 through the connector 232. The universal cord 23 propagates the illumination light emitted from the light source device 5 to the distal end portion 211 through the connector 233, the operating unit 22, and the flexible tube portion 213.

The voice input device 3 is input with a voice issued from vocal cords when the subject is the vocal cords. A distal end of a cord 31 is connected to the voice input device 3 and a connector 311 at the proximal end of the cord 31 is attachable to and detachable from the processing device 4. The voice input device 3 outputs the input voice to the processing device 4 through the cord 31 and the connector 311.

The processing device 4 performs predetermined image processing on an imaging signal in the subject which is captured by the imaging unit at the distal end portion 211 of the endoscope 2 and input through the universal cord 23. The processing device 4 controls each element of the endoscope system 1 based on various instruction signals transmitted from the switch units 223 in the operating unit 22 of the endoscope 2 through the universal cord 23.

The light source device 5 is formed by using a light source that emits pulse-shaped white light, a condenser lens, and the like. The light source device 5 supplies pulse-shaped white light from a white light source to the endoscope 2 connected through the connector 232 and the illumination fiber of the universal cord 23 as illumination light for illuminating inside of the subject which is a subject. A part of the pulsed light emitted from the light source device 5 is split at the connector 233 and formed into a pulse signal, and thereafter input into the processing device 4 through the branch cords 234 and 231 and the connector 232.

The display device 6 is formed by using a display using a liquid crystal or an organic EL (Electro Luminescence). The display device 6 displays various information including an image corresponding to a display image signal on which predetermined image processing is performed by the processing device 4 through an image cable 61. Thereby, an operator can observe a desired position in the subject and determine characteristics of the position by operating the endoscope 2 while seeing the image (in-vivo image) displayed by the display device 6.

Figure 2:
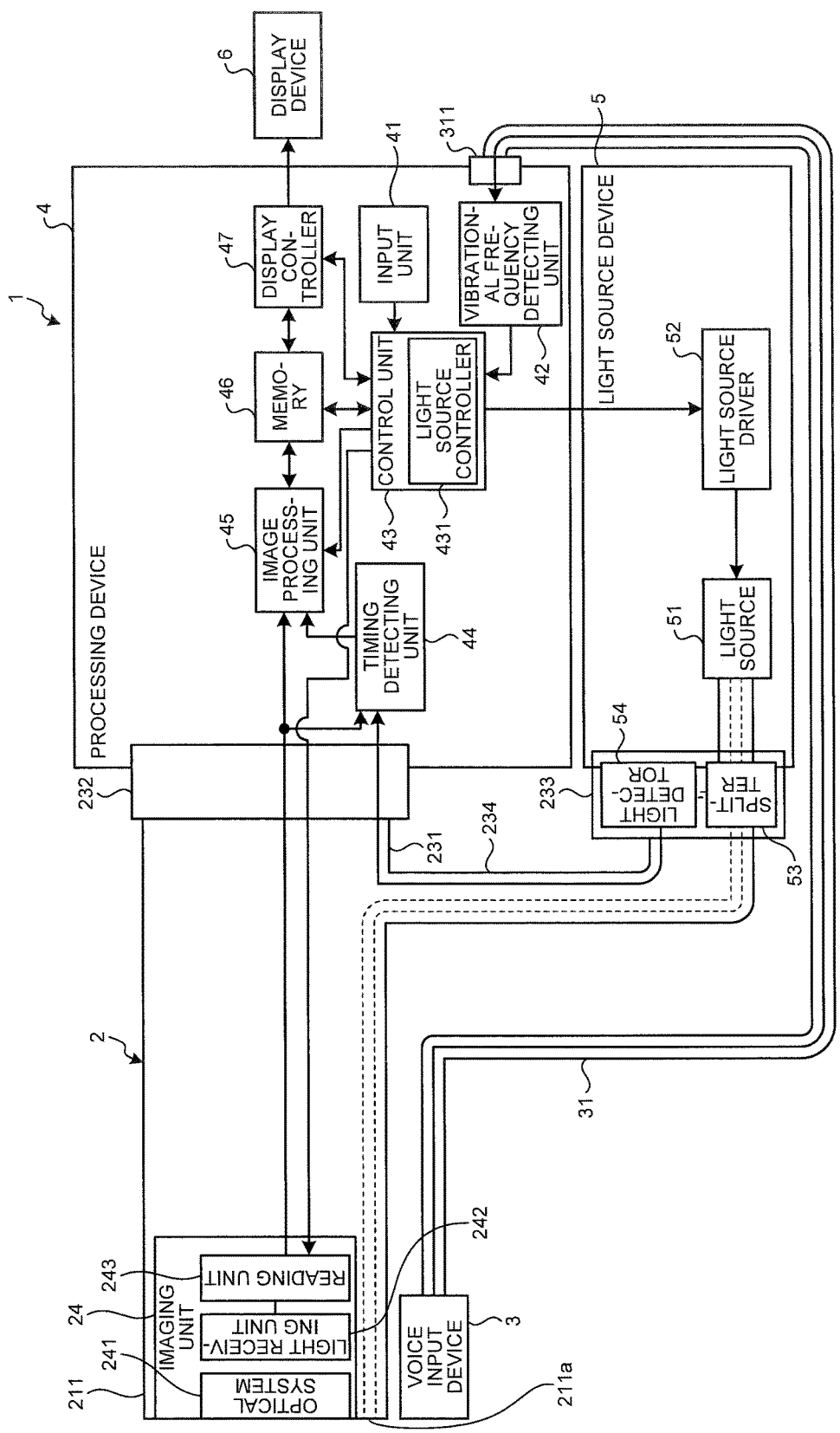
FIG. 2 is a block diagram schematically illustrating a configuration of the endoscope system illustrated in FIG. 1.

Next, configurations of the endoscope 2, the voice input device 3, the processing device 4, and the light source device 5, which are described in FIG. 1, will be described. FIG. 2 is a block diagram schematically illustrating the configuration of the endoscope system 1.

The endoscope 2 includes an imaging unit 24 at the distal end portion 211. The imaging unit 24 includes an optical system 241 such as an objective lens arranged on a light receiving surface side of a light receiving unit 242 described below, the light receiving unit 242 that generates a pixel signal representing the inside of the subject from an optical image formed on the light receiving surface, and a reading unit 243.

The light receiving unit 242 has a plurality of pixels arranged on the light receiving surface. The plurality of pixels is configured to receive light from the subject illuminated with the pulsed light from the light source device 5 and to perform photoelectric conversion on the received light to generate a pixel signal. A plurality of pixels is arranged in a matrix form on the light receiving unit 242. In the light receiving unit 242, a plurality of pixel rows (horizontal lines), in each of which two or more pixels are arranged along a horizontal direction, is arranged so as to be lined up in a vertical direction. The light receiving unit 242 generates a pixel signal representing the inside of the subject from the optical image formed on the light receiving surface.

The reading unit 243 performs exposure on the plurality of pixels in the light receiving unit 242 and reading of the pixel signal from the plurality of pixels. The light receiving unit 242 and the reading unit 243 are constituted by, for example, a CMOS image sensor and can perform exposure and reading for each horizontal line. The reading unit 243 performs an imaging operation, which performs exposure and reading, from a first horizontal line and generates a pixel signal by a rolling shutter method that performs charge reset, exposure, and reading by shifting timing for each horizontal line. Therefore, in the imaging unit 24, even in one imaging period (frame), the exposure timing and the read timing vary for each horizontal line. The reading unit 243 outputs the pixel signal read from the plurality of pixels of the light receiving unit 242 to the processing device 4 through a cable (not illustrated in the drawings) and the connector 232. A vertical synchronizing signal and a horizontal synchronizing signal attached to the pixel signal output from the CMOS image sensor are also input into a timing detecting unit 44 described later.

Next, the processing device 4 will be described. The processing device 4 includes an input unit 41, a vibrational frequency detecting unit 42, a control unit 43, a timing detecting unit 44, an image processing unit 45 (signal processing unit), a memory 46, and a display controller 47.

The input unit 41 is realized by using operation devices such as a mouse, a keyboard, and a touch panel and receives input of various instruction information of the endoscope system 1. Specifically, the input unit 41 receives subject information (for example, ID, date of birth, and name), identification information (for example, ID and examination corresponding items) of the endoscope 2, and various instruction information such as examination content.

The vibrational frequency detecting unit 42 detects the frequency of a voice which is input into the voice input device 3 and input into the processing device 4 through the cord 31 and the connector 311. The voice is issued from vocal cords which are the subject. The vibrational frequency detecting unit 42 outputs the detected frequency of the voice to the control unit 43.

The control unit 43 is realized by using a CPU and the like. The control unit 43 controls a processing operation of each element of the processing device 4. The control unit 43 controls operation of the processing device 4 by transmitting instruction information and data to each element of the processing device 4. The control unit 43 is connected to the imaging unit 24 and the light source device 5 through each cable. The control unit 43 includes a light source controller 431 that controls operation of the light source device 5. The light source controller 431 controls an illumination timing and an illumination period of the pulsed light from a light source 51 in synchronization with the frequency of the voice detected by the vibrational frequency detecting unit 42. The control unit 43 also controls operation of the imaging unit 24.

The timing detecting unit 44 detects the illumination timing and the illumination period of the pulsed light based on a pulse signal which is input from the light source device 5 and which corresponds to the pulsed light from the light source device 5. The timing detecting unit 44 detects the read, timing of the pixel signal read by the reading unit 243 for each horizontal line based on the vertical synchronizing signal and the horizontal synchronizing signal attached to the pixel signal output from the imaging unit 24. The timing detecting unit 44 acquires the read timing, the illumination timing, and the illumination period and detects a horizontal line, where the read timing overlaps with an illumination period in which an illumination time pixel signal described later is generated, as an overlap line from among the pixel signals read by the reading unit 243.

The image processing unit 45 performs predetermined image processing on the pixel signal of a plurality of pixels read by the reading unit 243 of the imaging unit 24. For example, the image processing unit 45 performs image processing including at least optical black subtraction processing, white balance (WB) adjustment processing, image signal synchronization processing when the image sensor is a Bayer array, color matrix calculating processing, gamma correction processing, color reproduction processing, and edge enhancement processing on the pixel signal.

The image processing unit 45 generates the illumination time pixel signal which is a pixel signal in a case in which a plurality of pixels is exposed in the illumination period of the pulsed light from the light source device 5 from the pixel signal of a plurality of pixels read by the reading unit 243 of the imaging unit 24 according to an overlapping state between the illumination timing and the illumination period of the pulsed light of the light source device 5 and the read timing of the pixel signal read by the reading unit 243. The image processing unit 45 generates the illumination time pixel signal corresponding to the illumination period of illumination for each frame for each illumination timing from pixel signals of a plurality of continuous frames stored in the memory 46 described later. For the overlap line, the image processing unit 45 generates the illumination time pixel signal based on a pixel signal of the overlap line read at an overlap timing that overlaps with the illumination period of the pulsed light and a pixel signal of an overlap line in a pixel signal of a frame that is read first after the overlap timing. For a non-overlap line which is a horizontal line other than the overlap line, the image processing unit 45 generates the illumination time pixel signal based on a pixel signal of a non-overlap pixel line in a pixel signal of a frame that is read first after the illumination period of the pulsed light in which the illumination time pixel signal is generated.

The memory 46 is realized by using volatile memory and/or non-volatile memory and stores various programs to operate the processing device 4 and the light source device 5. The memory 46 temporarily records information that is being processed by the processing device 4. The memory 46 stores the pixel signal read by the reading unit 243 for each frame in accordance with a matrix arrangement of a plurality of pixels in the light receiving unit 242. The memory 46 stores the illumination time pixel signal generated by the image processing unit 45 for each frame. The memory 46 may be formed by using a memory card or the like attached from the outside of the processing device 4.

The display controller 47 generates display image data to be displayed by the display device 6 from the illumination time pixel signals of a plurality of frames generated by the image processing unit 45 in accordance with a display cycle of the display device 6. The display controller 47 selects display image data from among the illumination time pixel signals of a plurality of frames generated by the image processing unit 45 for each display cycle of the display device 6. Alternatively, the display controller 47 generates a display image signal by synthesizing the illumination time pixel signals of a plurality of frames generated by the image processing unit 45 for each display cycle of the display device 6. The display controller 47 converts the display image data from a digital signal to an analog signal, changes image data of the converted analog signal into a high-definition television format or the like, and then outputs the image data to the display device 6.

Next, the light source device 5 will be described. The light source device 5 includes the light source 51 and a light source driver 52.

The light source 51 is formed by using a light source such as a white LED that emits pulse-shaped white light and an optical system such as a condenser lens. The light source 51 generates the illumination light to be supplied to the endoscope 2.

The light source driver 52 supplies a predetermined electric power to the light source 51 under control of the light source controller 431. Thereby, the light generated from the light source 51 is emitted to the subject from an illumination window 211*a* of the distal end portion 211 of the insertion unit 21 through the connector 233 and the universal cord 23. The imaging unit 24 is arranged near the illumination window 211*a*.

Figure 3:
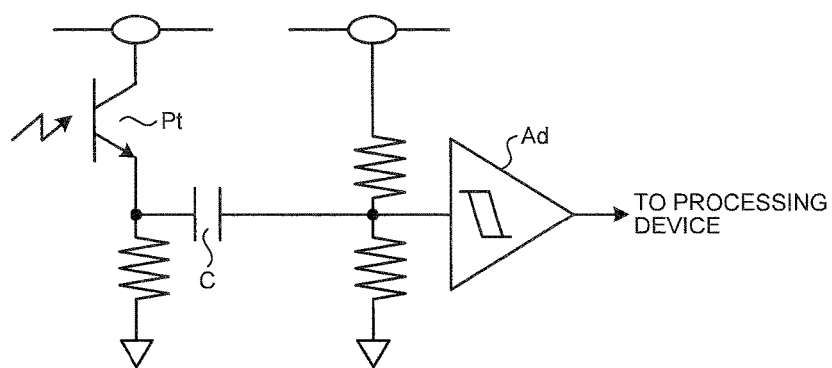
FIG. 3 is a diagram illustrating an example of a configuration of an electric circuit constituting alight detector illustrated in FIG. 2.

The connector 233 includes a splitter 53 for splitting a part of the pulsed light generated from the light source 51 and inputs the split light into a light detector 54 and the light detector 54 that converts the pulsed light input from the splitter 53 into a pulse signal. The splitter 53 is formed by an optical system such as a prism. The light detector 54 inputs the converted pulse signal into the timing detecting unit 44 of the processing device 4 through the branch cords 234 and 231 and the connector 232. FIG. 3 is a diagram illustrating an example of a configuration of an electric circuit constituting the light detector 54. As illustrated in FIG. 3, when the pulsed light enters into the light detector 54, a phototransistor Pt becomes an ON state and an electric current is input into an amplifier Ad through a capacitor C. Thereafter, a DC component is removed from the electric current and the electric current is amplified by the amplifier Ad, so that a pulse signal corresponding to the pulsed light is input into the processing device 4.

Figure 4:
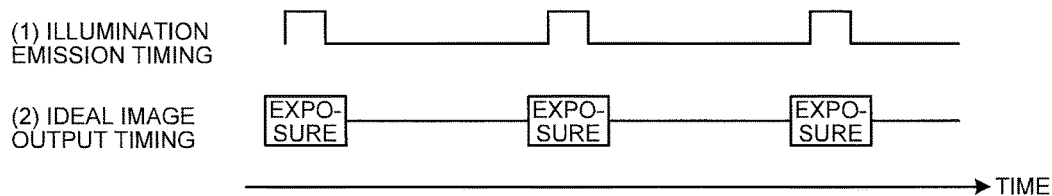
FIG. 4 is a timing chart illustrating an ideal image output timing in an imaging unit with respect to an illumination timing of pulsed light.

FIG. 4 is a timing chart illustrating an ideal image output timing in the imaging unit 24 with respect to the illumination timing of the pulsed light. As illustrated in FIG. 4, when each illumination timing of pulsed light (see FIG. 4 (1)) corresponds with each exposure timing in the imaging unit 24 (see FIG. 4 (2)), variation of brightness does not occur between a plurality of images to be output. On the other hand, in the first embodiment, the illumination timing of the pulsed light of the light source 51 is controlled so as to be synchronized with the vibration frequency of a voice issued from vocal cords which are the subject, so that the illumination timing of the pulsed light does not necessarily correspond with the exposure timing in the imaging unit 24. In the first embodiment, a case will be described in which a light emitting cycle of the pulsed light is longer than a frame cycle of the imaging unit 24 and a display cycle in the display device 6. First, with reference to FIG. 5, the illumination timing of the pulsed light by the light source 51 and the exposure timing and the read timing of the reading unit 243 will be described.

Figure 5:
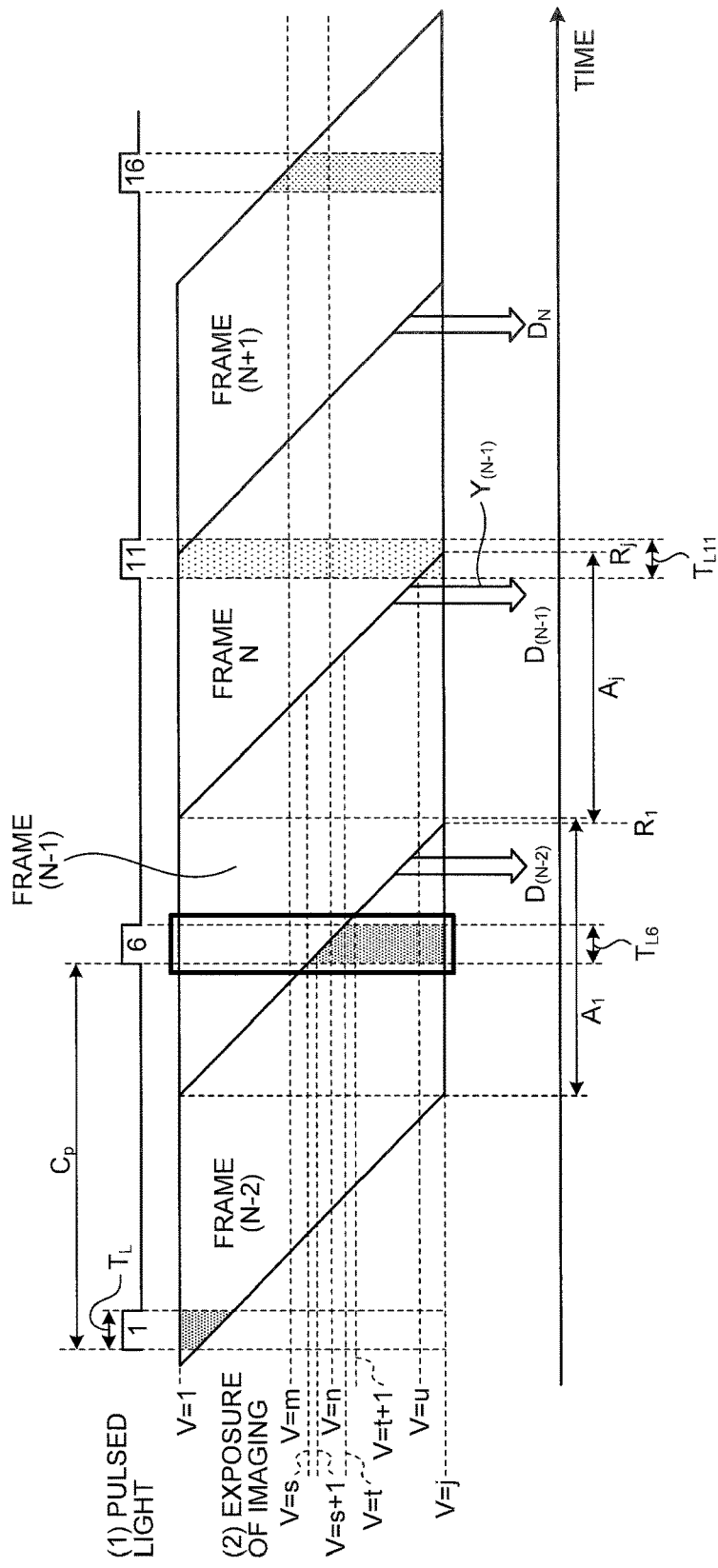
FIG. 5 is a diagram for explaining an illumination timing of pulsed light by a light source device and exposure and read timings by a reading unit illustrated in FIG. 2.

FIG. 5 is a diagram for explaining the illumination timing of the pulsed light by the light source 51 and the pixel exposure timing and the pixel signal read timing of the reading unit 243. (1) of FIG. 5 is a diagram illustrating an example of a timing chart illustrating the illumination timing of the pulsed light emitted from the light source 51. (2) of FIG. 5 is a diagram illustrating an example of a timing chart for explaining the exposure timing and the read timing for a plurality of pixels by the reading unit 243. Each pulsed light is output with the same pulse width (illumination period).

The illumination timing of pulsed light L emitted from the light source 51 is controlled so as to be synchronized with the vibration frequency of a voice issued from vocal cords which are the subject. For example, the pulsed light L is emitted from the light source 51 for each cycle $C_p$ illustrated in (1) of FIG. 5 during a period $T_L$.

The imaging unit 24 uses a rolling shutter method that changes the exposure timing and the read timing for each horizontal line V (V is an integer. V=1, . . . , m, . . . , s, . . . , n, . . . , t, . . . , u, . . . , j). Therefore, even for the pixel signals of the same frame, the exposure period and the read timing vary for each horizontal line. For example, for the pixels in the first horizontal line 1 of a frame (N −1), the reading unit 243 reads the pixel signal at a time $R_1$ after performing exposure in a period $A_1$. The reading unit 243 performs exposure and reading on the pixels of the following horizontal lines while shifting the timing in a time direction for each horizontal line. For the pixels in the last horizontal line j, the reading unit 243 performs exposure in a period $A_j$ and reads the pixel signal at a time $R_j$. The pixel signal $D_{(N-1)}$ of the frame (N−1) illustrated in FIG. 5 is generated when the exposure on each horizontal line from the first line 1 to the last line j is sequentially performed and the pixel signals of the horizontal lines V are read in order from the first line in a period from the time $R_1$ to the time $R_j$ as illustrated by an arrow $Y_{(N-1)}$.

When the rolling shutter method is employed in this way, even in the same frame, the exposure period is temporally shifted between the horizontal lines, so that if the light emitting cycle of the pulsed light from the light source 51 does not correspond with the frame cycle of the imaging unit 24, a plurality of frames may be exposed with one time illumination of the pulsed light. As a result, even in the same horizontal lines, the number of times of illumination and the illumination period vary between frames and brightness variation occurs for each horizontal line between frames.

For example, in the example of FIG. 5, the light emitting cycle of the pulsed light is longer than the frame cycle of the imaging unit 24, so that the illumination period $T_{L6}$ of the pulsed light $L_6$ overlaps with the exposure period of the first half horizontal lines in the frame (N−1) and the exposure period of the second half horizontal lines in the frame (N−2). As a result, regarding the pixel signal $D_{(N-1)}$ of the frame (N−1), an upper area (horizontal lines 1 to s) where all the pulsed light $L_6$ is exposed is bright, a central area (horizontal lines (s+1) to t) where only a part of the pulsed light $L_6$ is exposed gradually becomes dark (gradation), the next area (horizontal lines (t+1) to u) where no pulsed light is exposed becomes pitch-dark, and the lowest area (horizontal lines (u+1) to j) where a part of the next pulsed light $L_{11}$ is exposed gradually becomes bright (gradation). The first part and the last part of the illumination period $T_{L11}$ of the pulsed light $L_{11}$ following the pulsed light $L_6$ overlap with the exposure period of the frame (N−1) and the exposure period of the frame (N+1). However, the illumination period $T_{L11}$ is almost included in the exposure period of the frame N. Therefore, although the pixel signal $D_N$ of the frame N becomes a little dark in upper and lower partial areas, the pixel signal $D_N$ of the frame N becomes bright in the other area.

In the first embodiment, the pixel signal of each frame where the brightness varies due to differences of the number of times of illumination and the illumination period between frames even in the same horizontal lines is not output without change, but the image processing unit 45 of the processing device 4 generates the illumination time pixel signal, which is a pixel signal generated when all the pixels of the light receiving unit 242 are exposed at the illumination timing of the pulsed light, from pixel signals of a plurality of frames, so that a pixel signal where the brightness variation is removed is output.

Therefore, generation processing of the illumination time pixel signal in the processing device 4 will be described using an example in which an illumination time pixel signal corresponding to a pixel signal in a case in which all the pixels of the light receiving unit 242 are exposed with the pulsed light $L_6$ of FIG. 5 (1) is generated.

First, in the processing device 4, the timing detecting unit 44 detects the illumination timing and the illumination period of the pulsed light from the light source 51 and the read timing of each horizontal line of the light receiving unit 242 by the reading unit 243, and detects a horizontal line, where the read timing overlaps with an illumination period in which the illumination time pixel signal is generated, as an overlap line from among the pixel signals read by the reading unit 243. Further, the timing detecting unit 44 detects a horizontal line, where the read timing does not overlap with the illumination period in which the illumination time pixel signal is generated, as a non-overlap line from among the pixel signals read by the reading unit 243.

In the example of FIG. 5, the timing detecting unit 44 detects the first horizontal line 1 to the horizontal line s as non-overlap lines where the illumination period $T_{L6}$ of the pulsed light $L_6$ does not overlap with the read timing of both the pixel signal $D_{(N-2)}$ of the frame (N−2) and the pixel signal $D_{(n-1)}$ of the frame (N−1). The timing detecting unit 44 detects the horizontal line (s+1) to the horizontal line t as overlap lines where the illumination period $T_{L6}$ of the pulsed light $L_6$ overlaps with the read timing of the pixel signal $D_{(N-2)}$ of the frame (N−2). The timing detecting unit 44 detects the horizontal line (t+1) to the horizontal line j as non-overlap lines where the illumination period $T_{L6}$ of the pulsed light $L_6$ does not overlap with the read timing of any frame.

The generation of the illumination time pixel signal in the horizontal line 1 to the horizontal line s, which are the non-overlap lines, will be described. For example, the horizontal line m (1≤m≤s) will be described as an example. For the horizontal line m, the entire illumination period $T_{L6}$ of the pulsed light $L_6$, in which the illumination time pixel signal is generated, is included in the exposure period of the horizontal line m of the frame (N−1). For the horizontal line m, no pulsed light other than the pulsed light $L_6$ is emitted in the exposure period of the frame (N−1). Therefore, the pixel signal of the horizontal line m of the frame (N−1) read after the illumination of the pulsed light $L_6$ is a pixel signal in a case in which all the pixels located in the horizontal line m are exposed in the illumination period $T_{L6}$ of the pulsed light $L_6$. Therefore, the image processing unit 45 applies data of each pixel of the horizontal line m of the pixel signal $D_{(N-1)}$ of the frame (N−1) without change as a pixel signal (illumination time pixel signal) in a case in which the pixels of the horizontal line m are exposed in the illumination period of the pulsed light $L_6$. Specifically, the image processing unit 45 calculates the illumination time pixel signal by using the formula (1) for each pixel x of the horizontal line m.

(Pixel x of m-th line exposed with pulsed light $L_6$) =     (1)

(Pixel x of m-th line (exposed with pulsed light $L_6$) of $D_{(N-1)}$)

In the same manner, in the horizontal lines (t+1) to j which are non-overlap lines, the entire illumination period $T_{L6}$ of the pulsed light $L_6$, in which the illumination time pixel signal is generated, is included in the exposure period of the frame (N−2) and pulsed light other than the pulsed light $L_6$ is not irradiated in the exposure period of the frame (N−2). Therefore, each pixel signal of the horizontal lines (t+1) to j of the frame (N−2) read after the illumination of the pulsed light $L_6$ is a pixel signal in a case in which all the pixels located in the horizontal lines (t+1) to j at the illumination timing of the pulsed light $L_6$ are exposed. Therefore, the image processing unit 45 applies data of each pixel of each horizontal line of the pixel signal $D_{(N-2)}$ of the frame (N −2) without change as the illumination time pixel signal of the pulsed light $L_6$ of the horizontal lines (t+1) to j.

In this way, for a horizontal line which is a non-overlap line, the image processing unit 45 generates the illumination time pixel signal based on a pixel signal of a non-overlap pixel row of a frame that is read at read timing immediately after the illumination timing of the pulsed light, where the illumination time pixel signal is generated.

Next, the generation of the illumination time pixel signal in the horizontal lines (s+1) to t, which are the overlap lines, will be described by using the horizontal line n (s+1≤n≤t) as an example. The illumination period $T_{L_6}$ of the pulsed light $L_6$ overlaps with the read timing of the horizontal line n in the frame (N−2) and overlaps with both the exposure period of the horizontal line n of the frame (N−2) and the exposure period of the horizontal line n of the frame (N−1). For the horizontal line n, the other pulsed light is not irradiated neither in the exposure period of the horizontal line n of the frame (N−2) nor the exposure period of the horizontal line n of the frame (N−1). An output value of a pixel signal by pixels is proportional to a light receiving time in which light is actually received, so that the pixel signal (illumination time pixel signal) generated when the pixels in the horizontal line n are exposed in the illumination period of the pulsed light $L_6$ is a signal formed by directly synthesizing the pixel signal of the horizontal line n in the pixel signal $D_{(N−2)}$ of the frame (N−2) and the pixel signal of the horizontal line n in the pixel signal $D_{(N−1)}$ of the frame (N−1). Therefore, the image processing unit 45 calculates the illumination time pixel signal by using the formula (2) below for each pixel x of the horizontal line n.

(Pixel $x$ of $n$-$th$ line exposed with pulsed light $L_6$) =     (2)

(Pixel $x$ of $n$-$th$ line (exposed with pulsed light $L_6$) of $D_{(N−2)}$) +

(Pixel $x$ of $n$-$th$ line (exposed with pulsed light $L_6$) of $D_{(N−1)}$)

For a horizontal line to be an overlap line, the image processing unit 45 generates the illumination time pixel signal of an overlap pixel row by synthesizing a pixel signal of the overlap line that is read at an overlap timing that overlaps with the illumination period and a pixel signal of an overlap line in a pixel signal of a frame immediately after the overlap timing. The image processing unit 45 calculates the illumination time pixel signal by using the formula (1) or the formula (2) according to whether a pixel is located in an overlap line or a non-overlap line for each pixel, and outputs the calculated illumination time pixel signal as an image signal for each frame.

As described above, according to the first embodiment, the illumination time pixel signal, which is a pixel signal generated when a plurality of pixels is exposed in the illumination period of the pulsed light, is generated from a pixel signal that is read from a plurality of pixels according to the overlapping state between the illumination timing and the illumination period of the pulsed light by the light source 51 and the read timing of the pixel signal, so that even when the pulsed light is emitted at any timing with respect to the read timing of the image sensor, it is possible to eliminate variation of brightness between images to be output and maintain the image quality.

Figure 6:
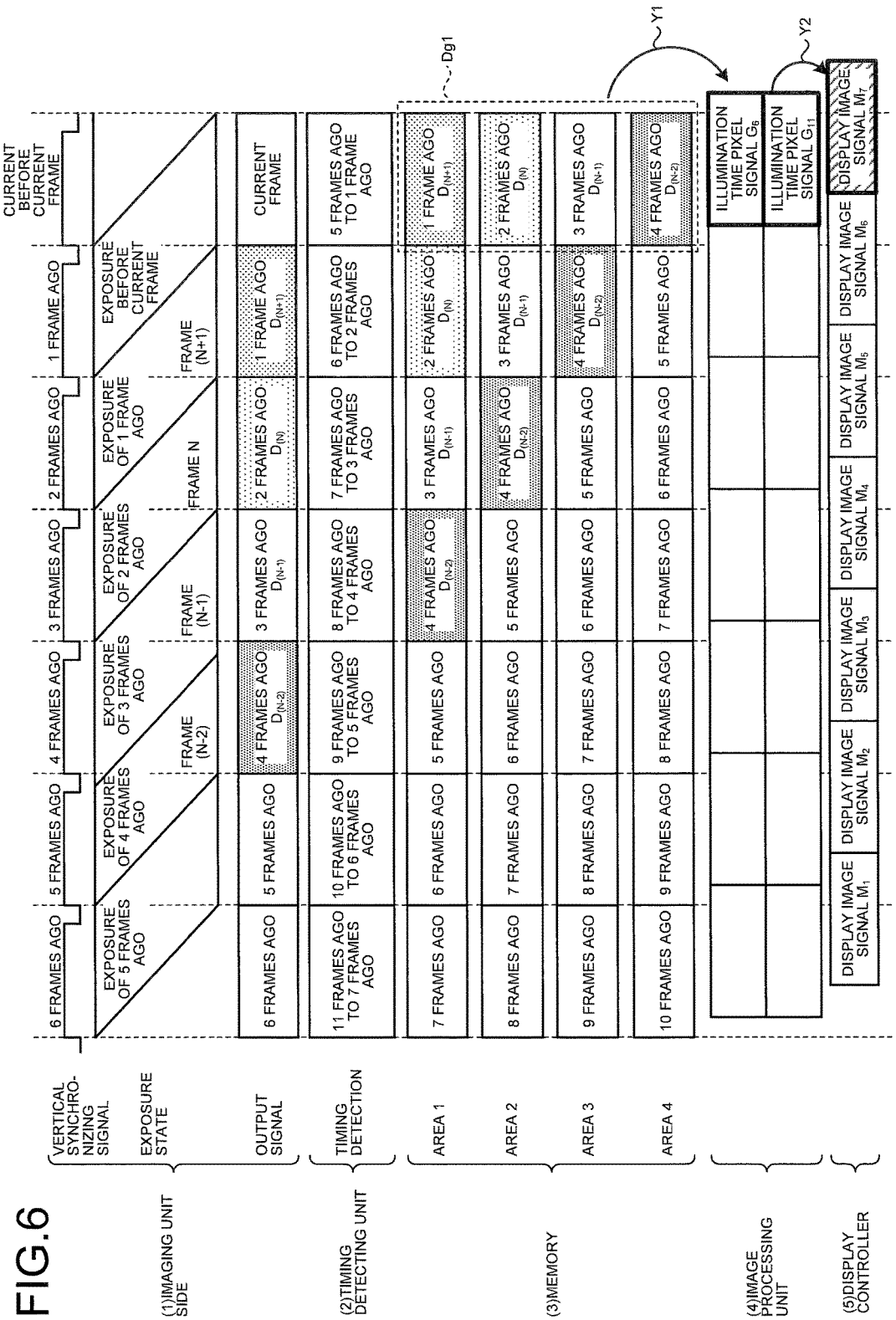
FIG. 6 is a timing chart illustrating a processing state of the imaging unit and each element of a processing device illustrated in FIG. 2.

In the processing device 4, for example, an algorism is employed in which a frame buffer using DDR3 with a large capacity is used as the memory 46, and when the image processing unit 45 performs calculation, pixel signals of a plurality of frames are processed in one frame period and an illumination time pixel signal of a plurality of frames is generated by performing pipeline processing in a state in which past pixel signals of a plurality of frames are read. (1) of FIG. 6 is a timing chart illustrating the vertical synchronizing signal in the CMOS image sensor included in the imaging unit 24, an exposure state of the CMOS image sensor, and data reading. (2) of FIG. 6 is a timing chart of data to be detected by the timing detecting unit 44. (3) of FIG. 6 is a timing chart of a pixel signal for each frame, which is stored in areas 1 to 4 of the memory 46. (4) of FIG. 6 is a timing chart of image processing in the image processing unit 45. (5) of FIG. 6 is a timing chart of display image data generation processing in the display controller 47.

As illustrated in (1) to (5) of FIG. 6, exposure and reading of a pixel signal are sequentially performed and read pixel data is sequentially output to the processing device 4 for each frame according to the timing of the vertical synchronizing signal by the imaging unit 24. In the example of (2) of FIG. 6, the timing detecting unit 44 processes pixel signals of five frames in one frame period. In the current frame period, the timing detecting unit 44 detects the read timings of a pixel signal from five frames ago to one frame ago and the illumination timings and the illumination periods from five frames ago to one frame ago. As illustrated in (3) of FIG. 6, in each area 1 to 4 of the memory 46, a pixel signal of one frame is stored, and a pixel signal to be stored is newly rewritten for each frame period. In the current frame period, pixel signals of five frames ago to two frames ago, which are stored in the areas 1 to 4, are respectively rewritten to pixel signals of four frames ago to one frame ago. As illustrated by an arrow Y1 in (4) of FIG. 6, in the current frame period, the image processing unit 45 reads a pixel signal Dg1 of four frames from four frames ago to one frame ago, which are stored in the areas 1 to 4 of the memory 46, generates an illumination time pixel signal, and outputs the generated illumination time pixel signal for each frame (illumination time pixel signals $G_6$ and $G_{11}$). The generation processing of the illumination time pixel signals $G_6$ and $G_{11}$ in the image processing unit 45 is the same as that described in the description with reference to FIG. 5. The number of frames of the illumination time pixel signal G generated at one time in the image processing unit 45 is not limited to a constant number of frames, but varies according to the number of times of emission of the pulsed light with respect to the frame cycle.

Next, as illustrated in (5) of FIG. 6, the display controller 47 generates display image signals $M_1$ to $M_7$ to be displayed by the display device 6 from the illumination time pixel signal generated by the image processing unit 45 in accordance with the display cycle of the display device 6. The display controller 47 generates the display image signal $M_7$ from the illumination time pixel signals $G_6$ and $G_{11}$ generated by the image processing unit 45 as illustrated by an arrow Y2 for a display cycle corresponding to the current frame period. The generation processing of the display image signal by the display controller 47 will be described with reference to FIGS. 7 and 8.

Figure 7:
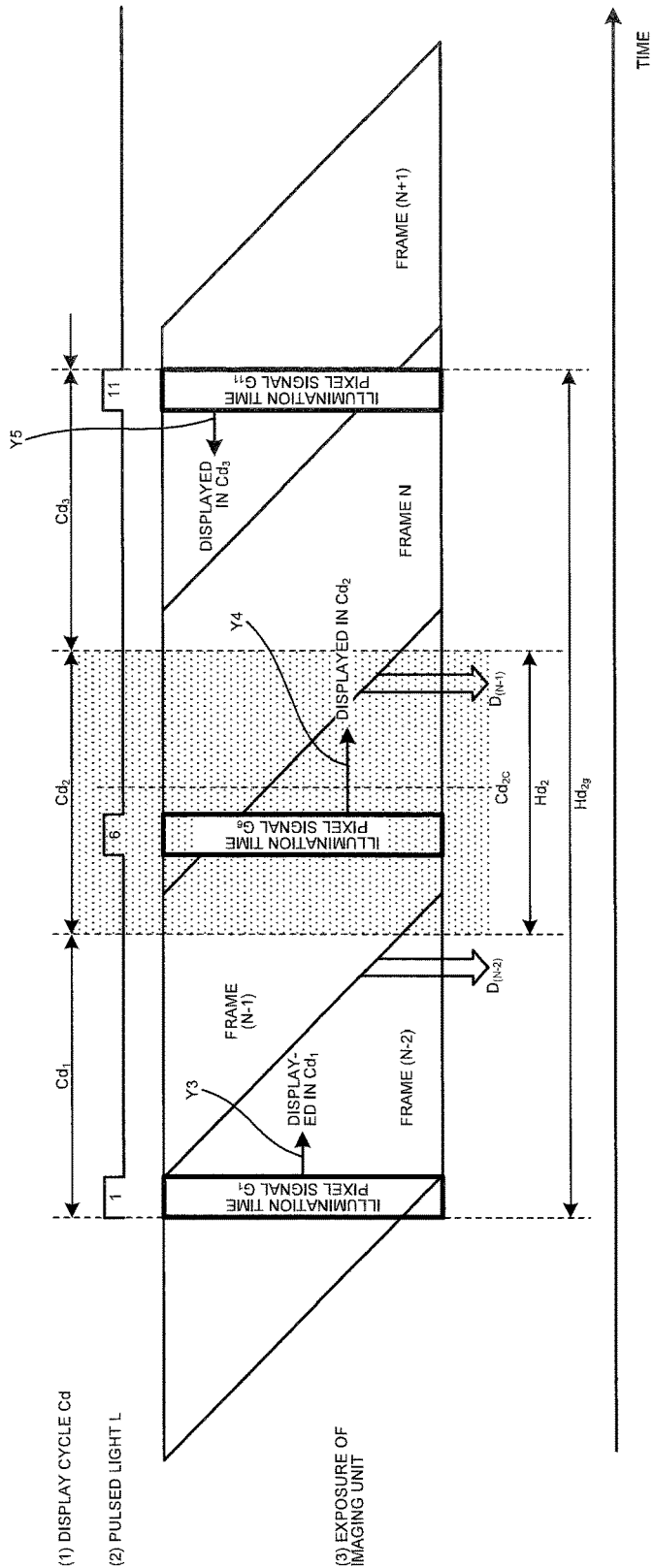
FIG. 7 is a diagram for explaining generation processing of a display image signal by a display controller illustrated in FIG. 2.
Figure 8:
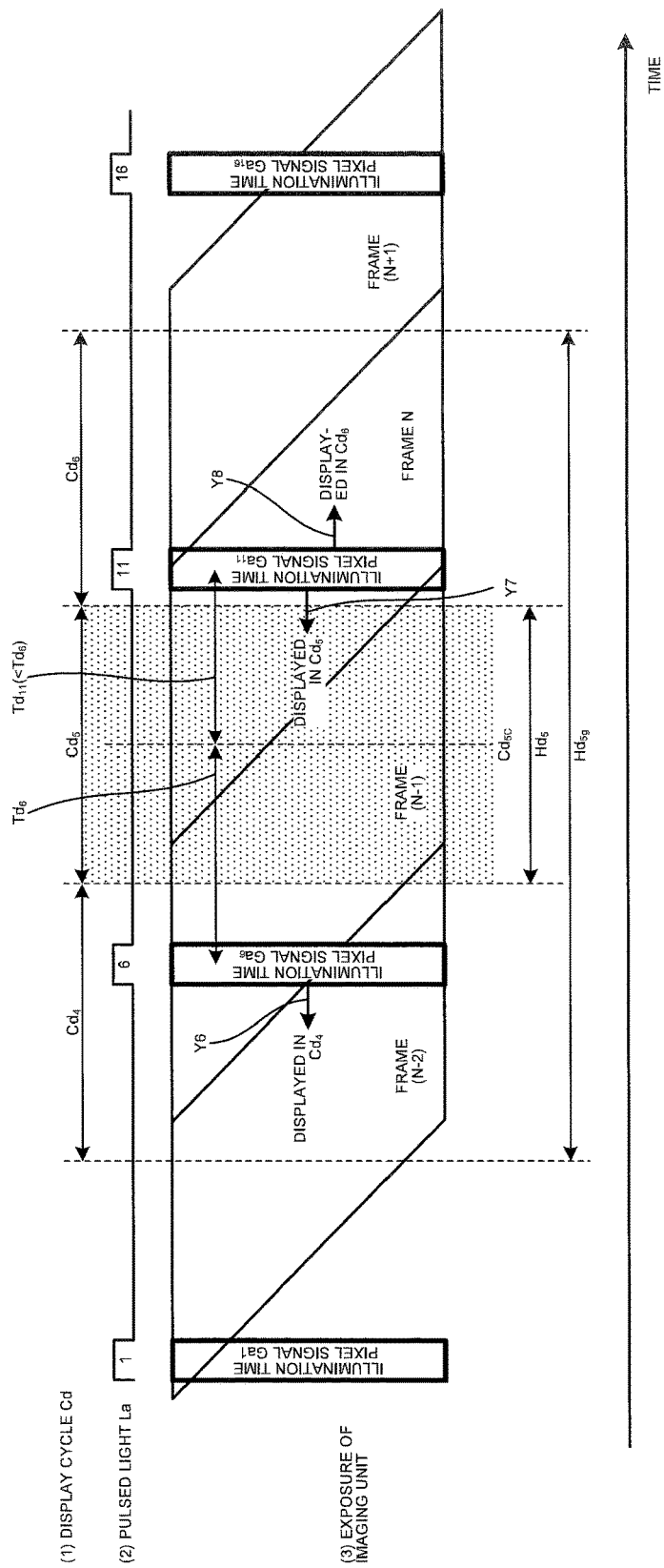
FIG. 8 is a diagram for explaining the generation processing of the display image signal by the display controller illustrated in FIG. 2.

FIGS. 7 and 8 are diagrams for explaining the generation processing of the display image signal by the display controller 47. (1) of FIG. 7 and (1) of FIG. 8 are timing charts illustrating the display cycle of the display device 6. (2) of FIG. 7 and (2) of FIG. 8 are an example of a timing chart illustrating the illustration timing of the pulsed light emitted from the light source 51. (3) of FIG. 7 and (3) of FIG. 8 are an example of a timing chart for explaining the exposure timing and the read timing of the reading unit 243. In FIGS. 7 and 8, for the purpose of explanation, the time axis of the illumination timing of the pulsed light corresponding to each illumination time pixel signal is moved to and overlapped on the time axis corresponding to the display cycle. FIG. 7 also schematically illustrates illumination time pixel signals $G_1$, $G_6$, and $G_{11}$ corresponding to the illumination timing of each pulsed light $L_1$, $L_6$, and $L_{11}$ generated in the image processing unit 45. FIG. 8 also schematically illustrates illumination time pixel signals $Ga_1$, $Ga_6$, $Ga_{11}$, and $Ga_{16}$ corresponding to the illumination timing of each pulsed light $La_1$, $La_6$, $La_{11}$, and $La_{16}$ generated in the image processing unit 45.

As illustrated in (1) of FIG. 7 and (1) of FIG. 8, the display device 6 outputs the display image signal in a display cycle Cd. Here, when the light emitting cycle of the pulsed light is longer than the display cycle, for each display cycle, there are cases in which the entire illumination period of the pulsed light is in the display cycle and a case in which only a part of the illumination period of the pulsed light is in the display cycle. In the example of FIG. 7, the display cycles $Cd_1$ to $Cd_3$ respectively include the illumination period of the pulsed light $L_1$, $L_6$, and $L_{11}$ corresponding to the illumination time pixel signals $G_1$, $G_6$, and $G_{11}$, so that the illumination time pixel signals $G_1$, $G_6$, and $G_{11}$ are directly selected and output as display image signals respectively corresponding to the display cycles $Cd_1$ to $Cd_3$. In other words, the display controller 47 causes the display device 6 to display the illumination time pixel signal $G_1$ as the display image signal for the display cycle $Cd_1$ (see arrow Y3). In the same manner, the display controller 47 causes the display device 6 to display the illumination time pixel signal $G_6$ as the display image signal for the display cycle $Cd_2$ (see arrow Y4) and causes the display device 6 to display the illumination time pixel signal $G_{11}$ as the display image signal for the display cycle $Cd_3$ (see arrow Y5). Alternatively, the display controller 47 may generate a signal obtained by synthesizing a plurality of illumination time pixel signals G as the display image signal. For example, when the display controller 47 generates the display image signal of the display cycle $Cd_2$, the display controller 47 enlarges an image employment range from a range $Hd_2$ corresponding to the display cycle $Cd_2$ to a range $Hd_{2g}$ that further includes the display cycles $Cd_1$ and $Cd_3$ before and after the display cycle $Cd_2$. Then, the display controller 47 employs the illumination time pixel signals $G_1$ and $G_{11}$ included in the range $Hd_{2g}$ along with the illumination time pixel signal $G_6$ and outputs an image signal that is synthesized with a weight according to a distance (time difference) between a central time $Cd_{2c}$ of the display cycle $Cd_2$ and a central time of the illumination period of the pulsed light of each illumination time pixel signal as the display image signal of the display cycle $Cd_2$.

On the other hand, in the example of FIG. 8, although the display cycles $Cd_4$ and $Cd_6$ of the display cycles $Cd_4$ to $Cd_6$ are corresponded with the illumination time pixel signals $Ga_6$ and $Ga_{11}$ according to the illumination periods of the pulsed light $La_6$ and $La_{11}$, no pulsed light is illuminated in the display cycle $Cd_5$ and there is no illumination time pixel signal corresponding to the display cycle $Cd_5$. Therefore, to generate the display image signal of the display cycle $Cd_5$, the display controller 47 enlarges an image employment range from a range $Hd_5$ corresponding to the display cycle $Cd_5$ to a range $Hd_{5g}$ that further includes the display cycles $Cd_4$ and $Cd_6$ before and after the display cycle $Cd_5$.

Subsequently, the display controller 47 compares distances (time differences) $Td_6$ and $Td_{11}$ ($<Td_6$) between the central time $Cd_{5c}$ of the display cycle $Cd_5$ and the central time of the pulsed light of each illumination time pixel signal $Ga_6$ and $Ga_{11}$ with respect to the illumination time pixel signals $Ga_6$ and $Ga_{11}$ corresponding in the range $Hd_{5g}$. Then, the display controller 47 causes the display device 6 to display the illumination time pixel signal $Ga_{11}$, where the distance is smaller, as a display image signal corresponding to the display cycle $Cd_5$ (arrow Y7). Alternatively, the display controller 47 generates an image signal obtained by synthesizing the illumination time pixel signals $Ga_6$ and $Ga_{11}$ included in the range $Hd_{5g}$ with a weight according to a distance (time difference) between the central time $Cd_{5c}$ of the display cycle $Cd_5$ and the central time of the illumination period of the pulsed light of each illumination time pixel signal as the display image signal corresponding to the display cycle $Cd_5$. Regarding the display cycles $Cd_4$ and $Cd_6$ which include the illumination periods of the pulsed light $La_6$ and $La_{11}$, the illumination time pixel signals $Ga_6$ and $Ga_{11}$ are caused to be displayed by the display device 6 as the display image signals of the display cycles $Cd_4$ and $Cd_6$ (see arrow Y6 and arrow Y8).

As described above, according to the first embodiment, even when the light emitting cycle of the pulsed light from the light source 51 does not correspond with the display cycle of the display device 6, the display image signal is generated according to the display cycle of the display device 6 from the illumination time pixel signal of a plurality of frames which are generated by the image processing unit 45 and which have no brightness variation and the display image signal is displayed by the display device 6, so that an effect is obtained that the image quality displayed on the display is good and images are smoothly and sequentially displayed without interruption.

Second Embodiment

Next, a second embodiment will be described. In the second embodiment, a case will be described in which the light emitting cycle of the pulsed light is shorter than the frame cycle of the imaging unit 24 and the display cycle of the display device 6. The endoscope system according to the second embodiment has the same configuration as that of the endoscope system according to the first embodiment.

Figure 9:
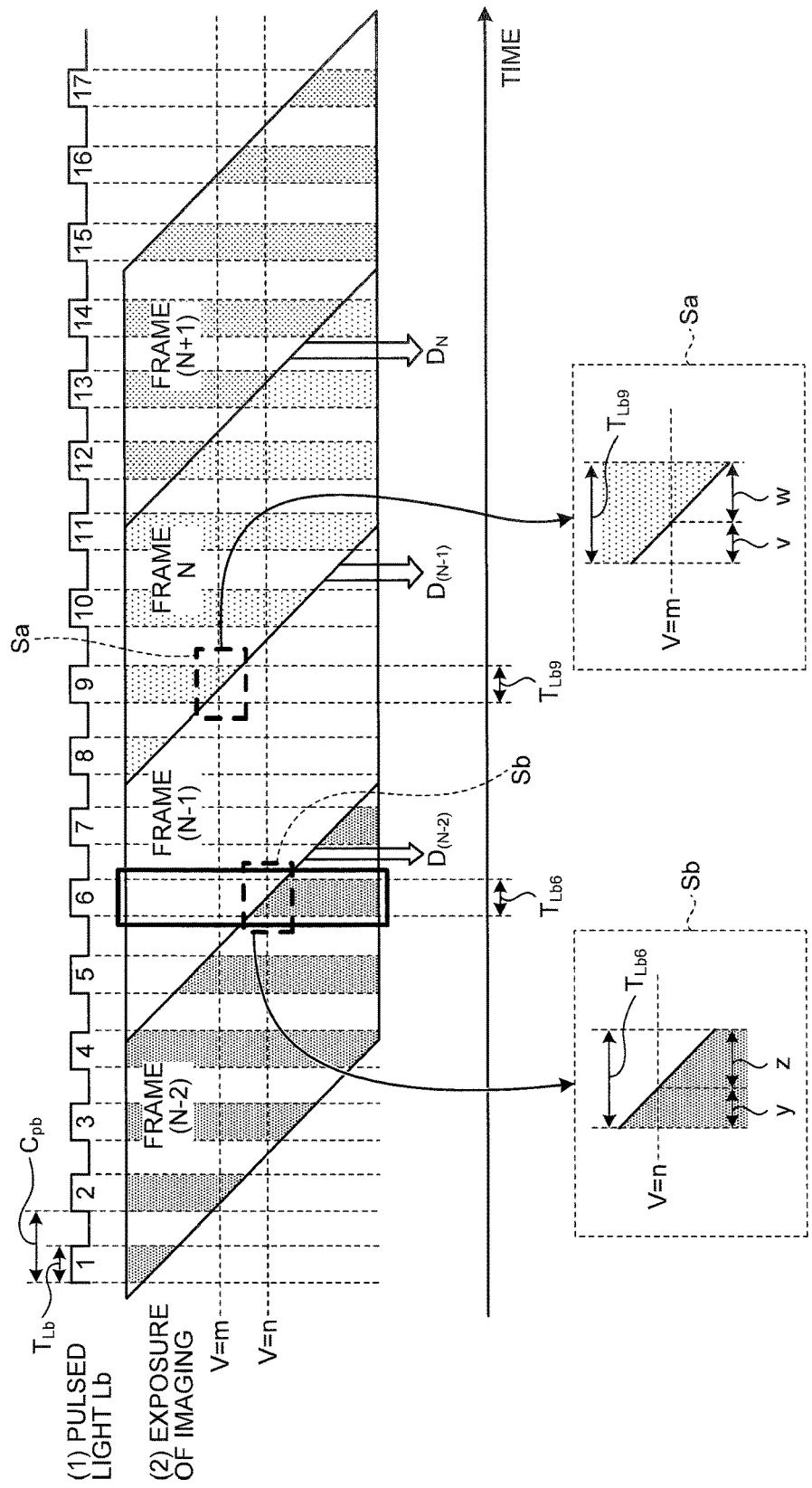
FIG. 9 is a diagram for explaining an illumination timing of pulsed light by a light source and exposure and read timings by a reading unit according to a second embodiment.

FIG. 9 is a diagram for explaining the illumination timing of the pulsed light by the light source 51 and the exposure timing and the read timing of the reading unit 243 when the endoscope system according to the second embodiment captures an image. (1) of FIG. 9 is a diagram illustrating an example of a timing chart illustrating the illumination timing of pulsed light Lb emitted from the light source 51. (2) of FIG. 9 is a diagram illustrating an example of a timing chart for explaining the exposure timing and the read timing of the reading unit 243. Each pulsed light is output with the same pulse width (illumination period).

As illustrated in (1) of FIG. 9, the pulsed light Lb is emitted from the light source 51 during a period $T_{Lb}$ at a cycle $C_{pb}$ shorter than the frame cycle of the imaging unit 24. In the example of FIG. 9, pulsed light is illuminated a plurality of times in the exposure period of any horizontal line, so that pixels in each horizontal line are multiply-exposed. Therefore, the image processing unit 45 performs calculation processing for generating the illumination time pixel signal by considering that the pixels in each horizontal line are multiply-exposed in addition that there is a line where the read timing and the illumination period overlap with each other. Specifically, as an example, a case will be described in which the image processing unit 45 generates an illumination time pixel signal corresponding to a pixel signal generated when all the pixels of the light receiving unit 242 are exposed with the pulsed light $Lb_6$ in (1) of FIG. 9.

First, the horizontal line m which is a non-overlap line will be described. For the horizontal line m which is a non-overlap line, the image processing unit 45 generates the illumination time pixel signal based on the pixel signal of the horizontal line m in the pixel signal $D_{(N-1)}$ of the frame (N−1) read at read timing immediately after the illumination period of the pulsed light $Lb_6$. However, the exposure period of the horizontal line m of the frame (N−1) includes the entire illumination period of the pulsed light $Lb_7$ and $Lb_8$ and a part of the illumination period $T_{Lb9}$ of the pulsed light $Lb_9$ in addition to the entire illumination period $T_{Lb6}$ of the pulsed light $Lb_6$. Therefore, the image processing unit 45 calculates the illumination time pixel signal by using the formula (3) which takes into account a ratio between the illumination period of the pulsed light $Lb_6$ and the illumination period of other pulsed light $Lb_7$, $Lb_8$, and $Lb_9$ for each pixel x of the horizontal line m. In the frame (N−1), a period in which the illumination period $T_{Lb9}$ of the pulsed light $Lb_9$ is included in the exposure period of the horizontal line m is defined as v and a period in which the illumination period $T_{Lb9}$ of the pulsed light $Lb_9$ is not included in the exposure period of the horizontal line m is defined as w (see area Sa).

$$\begin{aligned}(\text{Pixel } x \text{ of } m\text{-}th \text{ line exposed with pulsed light } Lb_6) = \quad (3)\\ \frac{(\text{Pixel } x \text{ of } m\text{-}th \text{ line}}{\text{(exposed with pulsed light } Lb_6 \text{ to } Lb_9) \text{ of } D_{(N-1)}) \times}\\ \frac{\text{Exposure period by pulsed light } Lb_6}{\text{Total exposure period by pulsed light } Lb_6 \text{ to } Lb_9} = \\ \text{in } m\text{-}th \text{ line of } D_{(N-1)} \\ (\text{Pixel } x \text{ of } m\text{-}th \text{ line (exposed with pulsed light } Lb_6 \text{ to } Lb_9) \\ \text{of } D_{(N-1)}) \times \frac{v+w}{4v+3w}\end{aligned}$$

Regarding the horizontal line n which is an overlap line, the image processing unit 45 generates the illumination time pixel signal based on the pixel signal of the horizontal line n in the pixel signal $D_{(N-2)}$ of the frame (N−2) read at an overlap timing overlapping with the illumination period of the pulsed light $Lb_6$ and the pixel signal of the horizontal line n in the pixel signal $D_{(N-1)}$ of the frame (N−1) immediately after the overlap timing. However, the exposure period of the horizontal line n of the frame (N−2) includes the illumination periods of the pulsed light $Lb_3$, $Lb_4$, and $Lb_5$ in addition to the first half of the illumination period $T_{Lb6}$ of the pulsed light $Lb_6$. The exposure period of the horizontal line n of the frame (N−1) includes the illumination periods of the pulsed light $Lb_7$, $Lb_8$, and $Lb_9$ in addition to the second half of the illumination period $T_{Lb6}$ of the pulsed light $Lb_6$. Therefore, the image processing unit 45 calculates the pixel signal of the horizontal line n in receiving only the pulsed light $Lb_6$ for the frame (N−2) and the frame (N−1), respectively, in view of ratios between the illumination period of the pulsed light $Lb_6$ and the illumination periods of other pulsed light for each pixel x of the horizontal line n, and synthesizes the calculation results.

Specifically, the image processing unit 45 calculates the illumination time pixel signal of each pixel x of the horizontal line n, which is an overlap line, by using the formula (4). In the frame (N−2), a period in which the illumination period $T_{Lb6}$ of the pulsed light $Lb_6$ is included in the exposure period of the horizontal line n is defined as y and a period in which the illumination period $T_{Lb6}$ of the pulsed light $Lb_6$ is not included in the exposure period of the horizontal line n is defined as z (see area Sb). Although not illustrated in the drawings, in the frame (N−1), a period in which the illumination period $T_{Lb9}$ of the pulsed light $Lb_9$ is included in the exposure period of the horizontal line n is defined as z and a period in which the illumination period $T_{Lb9}$ of the pulsed light $Lb_9$ is not included in the exposure period of the horizontal line n is defined as y. In the example described above, the calculations are performed on the assumption that the pulse widths (illumination periods) of all pulsed light are the same and (v+w)=(y+z) is established.

$$\begin{aligned}(\text{Pixel } x \text{ of } n\text{-}th \text{ line exposed with pulsed light } Lb_6) = \quad (4)\\ \frac{(\text{Pixel } x \text{ of } n\text{-}th}{\text{line(exposed with pulsed light } Lb_3 \text{ to } Lb_6) \text{of } D_{(N-2)}) \times}\\ \frac{\text{Exposure period by pulsed light } Lb_6}{\text{in } n\text{-}th \text{ line of } D_{(N-2)}} + \\ \frac{\text{in } n\text{-}th \text{ line of } D_{(N-2)}}{\text{Total exposure period by pulsed light } Lb_3 \text{ to } Lb_6} \\ (\text{Pixel } x \text{ of } n\text{-}th \text{ line(exposed with pulsed light } Lb_3 \text{ to } Lb_6) \\ \text{of } D_{(N-2)}) \times \frac{y}{4y+3z} + \\ (\text{Pixel } x \text{ of } n\text{-}th \text{ line(exposed with pulsed light } Lb_6 \text{ to } Lb_9) \\ \text{of } D_{(N-1)}) \times \frac{z}{3y-4z}\end{aligned}$$

Figure 10:
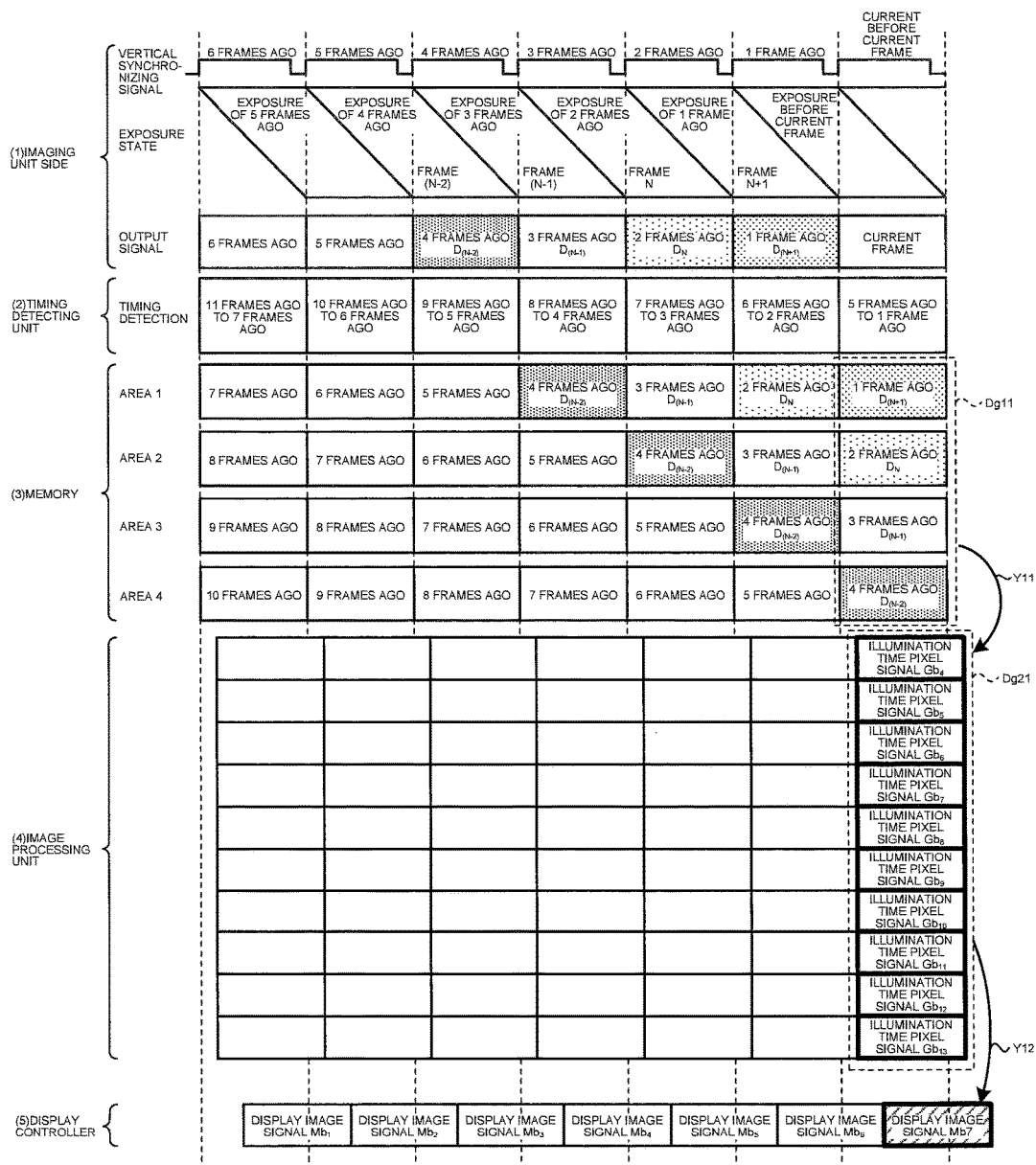
FIG. 10 is a timing chart illustrating a processing state of an imaging unit and each element of a processing device according to the second embodiment.

FIG. 10 is a timing chart illustrating a processing state of the imaging unit 24 and each element of the processing device 4 according to the second embodiment. (1) of FIG. 10 is a timing chart illustrating the vertical synchronizing signal in the CMOS image sensor included in the imaging unit 24, an exposure state of the CMOS image sensor, and data reading. (2) of FIG. 10 is a timing chart of data to be detected by the timing detecting unit 44. (3) of FIG. 10 is a timing chart of a pixel signal for each frame, which is stored in areas 1 to 4 of the memory 46. (4) of FIG. 10 is a timing chart of image processing in the image processing unit 45. (5) of FIG. 10 is a timing chart of display image data generation processing in the display controller 47. In the second embodiment, in the current frame period, a pixel signal Dg11 of four frames from four frames ago to one frame ago, which are stored in the areas 1 to 4 of the memory 46, is read, an illumination time pixel signal corresponding to each pulsed light is generated (see arrow Y11), and the illumination time pixel signal is output for each frame (illumination time pixel signals $Gb_4$ to $Gb_{13}$). In the same manner as in the first embodiment, the number of frames of the illumination time pixel signal G generated at one time in the image processing unit 45 is not limited to a constant number of frames, but varies according to the number of times of emission of the pulsed light with respect to the frame period.

Then, as illustrated in (5) of FIG. 10, the display controller 47 generates display image signals $Mb_1$ to $Mb_7$ to be displayed by the display device 6 from the illumination time pixel signal group Dg21 generated by the image processing unit 45 as illustrated by an arrow Y12 in accordance with the display cycle of the display device 6. The display controller 47 generates the display image signal $Mb_7$ from the illumination time pixel signals $Gb_4$ to $Gb_{13}$ generated by the image processing unit 45 for a display cycle corresponding to the current frame period. The generation processing of the display image signal by the display controller 47 will be described with reference to FIG. 11.

Figure 11:
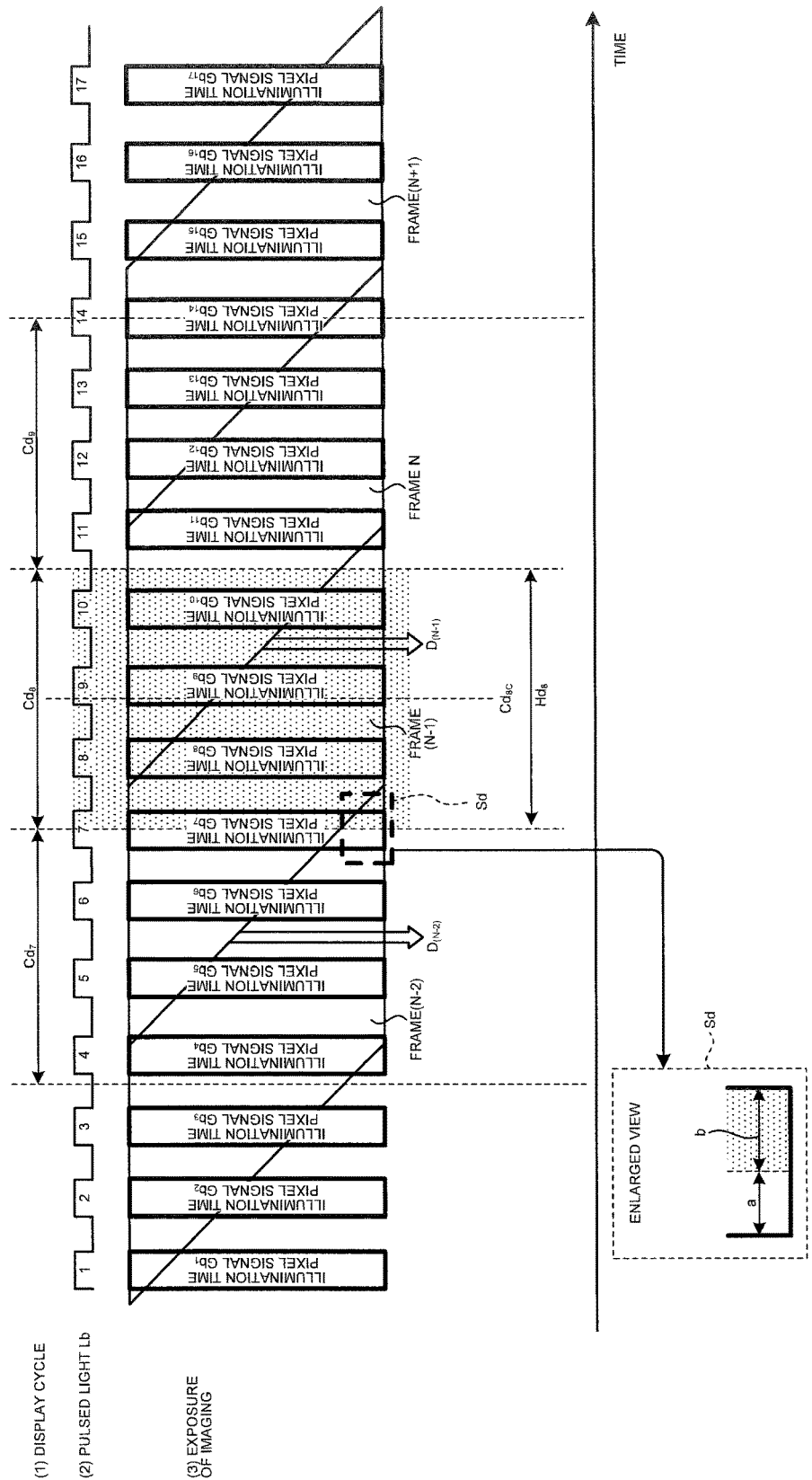
FIG. 11 is a diagram for explaining generation processing of a display image signal by a display controller according to the second embodiment.

FIG. 11 is a diagram for explaining the generation processing of the display image signal by the display controller 47 according to the second embodiment. (1) of FIG. 11 is a timing chart illustrating the display cycle of the display device 6. (2) of FIG. 11 is an example of a timing chart illustrating the illustration timing of the pulsed light emitted from the light source 51. (3) of FIG. 11 is an example of a timing chart for explaining the exposure timing and the read timing of the reading unit 243. In FIG. 11, for the purpose of explanation, the time axis of the illumination timing of the pulsed light corresponding to each illumination time pixel signal is moved to and overlapped on the time axis corresponding to the display cycle. FIG. 11 also schematically illustrates illumination time pixel signals $Gb_1$ to $Gb_{17}$ corresponding to the illumination timing of each pulsed light $Lb_1$ to $Lb_{17}$ generated in the image processing unit 45.

A case will be described in which a display image signal corresponding to the display cycle $Cd_8$ among the display cycles $Cd_7$ to $Cd_9$ illustrated in FIG. 11 is generated. A period $Hd_8$ corresponding to the display cycle $Cd_8$ includes illumination periods of the pulsed light $Lb_7$ to $Lb_{10}$ corresponding to the illumination time pixel signals $Gb_7$ to $Gb_{10}$. The display controller 47 generates the display image signal M corresponding to the display cycle $Cd_8$ by synthesizing the illumination time pixel signals $Gb_7$ to $Gb_{10}$. However, only a part of the illumination period corresponding to the illumination time pixel signal $Gb_7$ corresponds to the period $Hd_8$ corresponding to the display cycle $Cd_8$, so that a period in which the illumination period of the pulsed light $Lb_7$ is included in the period $Hd_8$ corresponding to the display cycle $Cd_8$ is defined as a and a period in which the illumination period of the pulsed light $Lb_7$ is not included in the period $Hd_8$ corresponding to the display cycle $Cd_8$ is defined as b (see area Sd). The illumination period (pulse width) of each pulsed light is uniform. Therefore, the display controller 47 generates the display image signal M corresponding to the display cycle $Cd_8$ by using the formula (5).

$$M = \frac{b \times Gb_7 + (a+b) \times Gb_8 + (a+b) \times Gb_9 + (a+b) \times Gb_{10}}{3a+b} \quad (5)$$

The display controller 47 may calculate the display image signal M corresponding to the display cycle $Cd_8$ by multiplying each data corresponding to the central time $Cd_{8c}$ of the display cycle $Cd_8$ by a weighting coefficient ($\alpha$, $\beta$, $\gamma$, $\delta$). Specifically, the display controller 47 generates the display image signal M corresponding to the display cycle $Cd_8$ by using the formula (6).

$$M = \frac{\alpha(a+b) \times Gb_7 + \beta(a+b) \times Gb_8 + \gamma(a+b) \times Gb_9 + \delta(a+b) \times Gb_{10}}{3a+b} \quad (6)$$

Therefore, the display controller 47 generates the display image signal by synthesizing, according to an exposure ratio, a plurality of illumination time pixel signals corresponding to all illumination timings included in the display cycle of a control target when overlapping the time axis of illumination timing of each illumination time pixel signal on the time axis of the display cycle. The weighting coefficient ($\alpha$, $\beta$, $\gamma$, $\delta$) may also be used when the control unit 43 controls brightness of the light source 51. As a result, it is possible to prevent insufficient amount of light and suppress brightness variation between frames during a stroboscopic observation in which an observation is performed by emitting pulsed light. Specifically, it is possible to brighten by establishing an inequality ($\alpha+\beta+\gamma+\delta$)≥1 and it is possible to darken by establishing an inequality ($\alpha+\beta+\gamma+\delta$)≤1. When setting the value of ($\alpha+\beta+\gamma+\delta$) to a fixed value, the brightness variation between frames is suppressed.

When the light emitting cycle of the pulsed light is shorter than the frame cycle of the imaging unit 24 and the display cycle of the display device 6 as in the second embodiment, the illumination time pixel signal may be calculated by considering whether each pixel is located in an overlap line or a non-overlap line and a ratio between an illumination period of pulsed light in which the illumination time pixel signal is generated and an illumination period of the other pulsed light included in the exposure period of the line. When the light emitting cycle of the pulsed light from the light source 51 is shorter than the display cycle of the display device 6 as in the second embodiment, the display image signal which is generated by the image processing unit 45 and in which a plurality of illumination time pixel signals are synthesized may be displayed by the display device 6 according to the display cycle of the display device 6. Thereby, also in the second embodiment, the same effect as that of the first embodiment is obtained.

Figure 12:
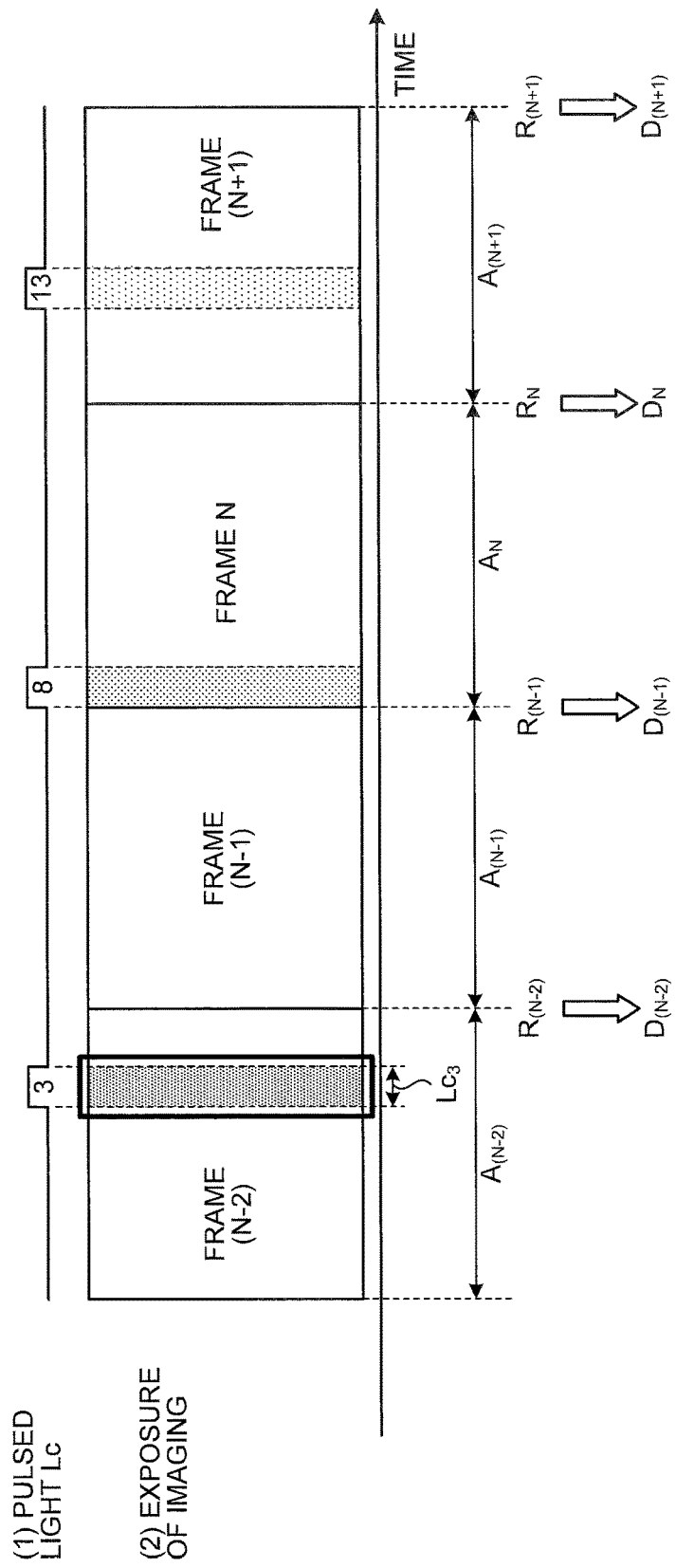
FIG. 12 is a diagram for explaining an illumination timing of pulsed light by a light source and exposure and read timings by a reading unit when a CCD image sensor is employed in the first and second embodiments.

The first and second embodiments can also be applied when employing a CCD (Charge Coupled Devices) image sensor, which performs imaging processing by a global shutter method, as the image sensor of the imaging unit 24. (1) of FIG. 12 is a diagram illustrating an example of a timing chart illustrating the illumination timing of pulsed light Lc emitted from the light source 51. (2) of FIG. 12 is a diagram illustrating an example of a timing chart for explaining the exposure timing and the read timing of the reading unit 243 when the image sensor of the imaging unit 24 is a CCD image sensor. Each pulsed light is output with the same pulse width (illumination period).

In the example of FIG. 12, the pulsed light Lc is emitted in a cycle longer than the frame cycle of the imaging unit 24. The imaging unit 24 employs the global shutter method, so that all the pixel signals of the light receiving unit 242 from the same frame are exposed in the same period and read at the same timing. For example, regarding the frame (N−2), after being exposed in an exposure period $A_{(N-2)}$, a pixel signal $D_{(N-2)}$ corresponding to a pixel signal of all the pixels is read at a time $R_{(N-2)}$. In the same manner, regarding the frame (N−1), the frame N, and the frame (N+1), after being exposed in exposure periods $A_{(N-1)}$, $A_N$, and $A_{(N+1)}$, respectively, pixel signals $D_{(N-1)}$, $D_N$, and $D_{(N+1)}$ corresponding to pixel signals of all the pixels are read at times $R_{(N-1)}$, $R_N$, and $R_{(N+1)}$. In the example of FIG. 12, each illumination period of the pulsed light Lc is not overlapped with the read timing of each pixel signal, so that in the same manner as the generation processing of the illumination time pixel signal with respect to a non-overlap line in the first embodiment, the illumination time pixel signal is generated based on a pixel signal of a non-overlap line in the pixel signal of a frame that is read immediately after the illumination period of the pulsed light in which the illumination time pixel signal is generated. For example, when generating an illumination time pixel signal corresponding to a pixel signal generated when all the pixels of the light receiving unit 242 are exposed with the pulsed light $Lc_3$ in (1) of FIG. 12, the illumination time pixel signal is calculated by using the formula (7) for each pixel x in any horizontal line V.

$$(\text{Pixel } x \text{ of } V\text{-}th \text{ line exposed with pulsed light } Lc_3) = \tag{7}$$
$$(\text{Pixel } x \text{ of } V\text{-}th \text{ line of } D_{(N-2)}(\text{exposed with pulsed light } Lc_3))$$

Although not illustrated in FIG. 12, regarding an illumination period that overlaps with the read timing of each pixel signal among each illumination period of the pulsed light Lc, for each pixel in any horizontal line, in the same manner as the generation processing of the illumination time pixel signal with respect to an overlap line in the first embodiment, an illumination time pixel signal of an overlap pixel row is generated by synthesizing a pixel signal of the overlap line that is read at an overlap timing overlapping with the illumination period and a pixel signal of an overlap line in a pixel signal of a frame immediately after the overlap timing.

The pixel signals $D_{(N-2)}$, $D_N$, and $D_{(N+1)}$ among the pixel signals $D_{(N-2)}$ to $D_{(N+1)}$ are darkish images because illumination of the pulsed light is performed once in each of the exposure periods $A_{(N-2)}$, $A_N$, and $A_{(N+1)}$. The pixel signal $D_{(N-1)}$ among the pixel signals $D_{(N-2)}$ to $D_{(N+1)}$ is a pitch-dark image without exposure because illumination of the pulsed light is not performed during the exposure period $A_{(N-1)}$. However, the illumination time pixel signal that is actually output from the image processing unit 45 corresponds to a pixel signal generated when all the pixels in the light receiving unit 242 are exposed with the pulsed light, so that no variation occurs in the brightness.

Figure 13:
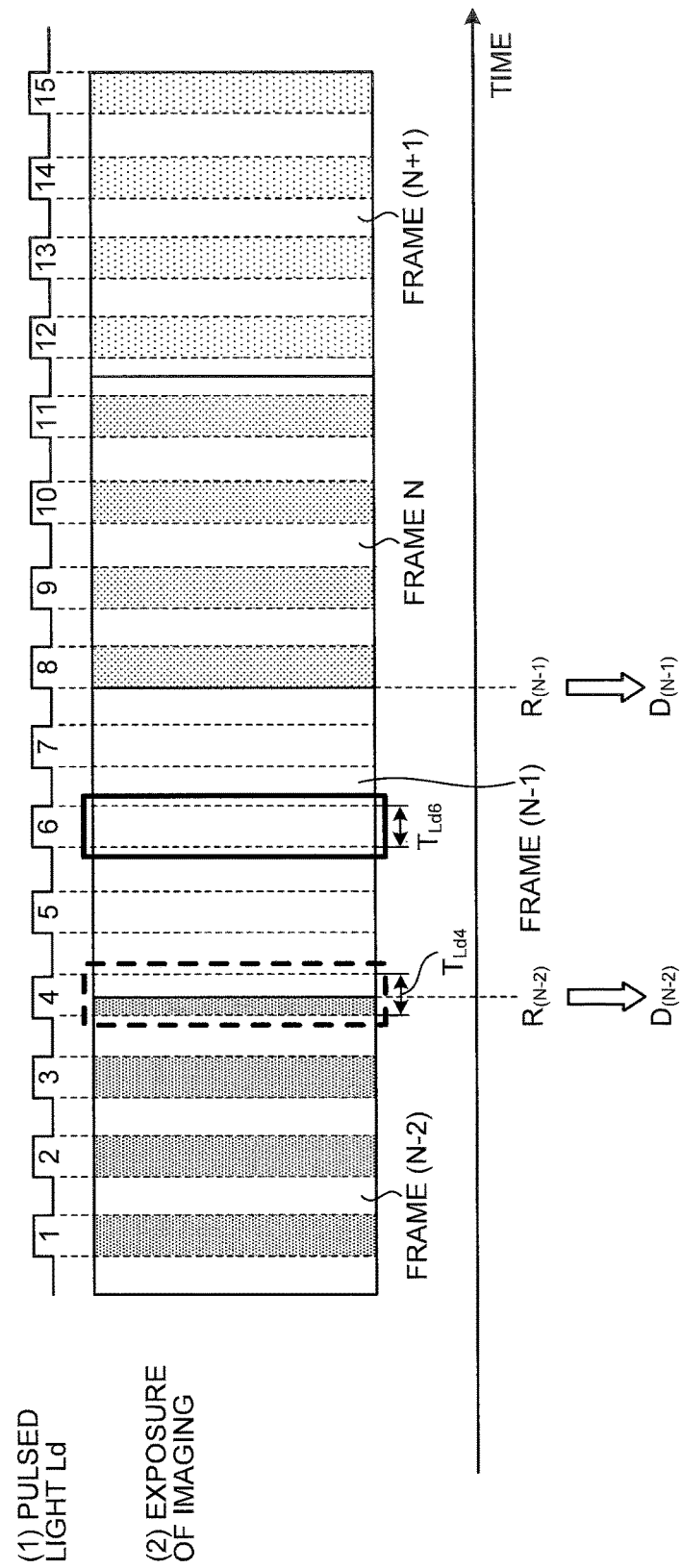
FIG. 13 is a diagram for explaining another example of an illumination timing of pulsed light by a light source and exposure and read timings by a reading unit when a CCD image sensor is employed in the first and second embodiments.

A case in which the pulsed light Ld is emitted in a cycle shorter than the frame cycle of the imaging unit 24 will be described with reference to FIG. 13. (1) of FIG. 13 is a diagram illustrating an example of a timing chart illustrating the illumination timing of the pulsed light Ld emitted from the light source 51. (2) of FIG. 13 is a diagram illustrating an example of a timing chart for explaining the exposure timing and the read timing of the reading unit 243 when the image sensor of the imaging unit 24 is a CCD image sensor. Each pulsed light is output with the same pulse width (illumination period).

For example, a case in which an illumination time pixel signal is generated for the pulsed light $Ld_6$ in (1) of FIG. 13 will be described. The illumination period $T_{Ld6}$ of the pulsed light $Ld_6$ does not overlap with the read timing of each pixel signal. In this case, for any horizontal line V, the illumination time pixel signal is generated based on the pixel signal of the horizontal line V corresponding to each of the pixel signals $D_{(N-1)}$ of the frame (N-1) that is read at the read timing immediately after the illumination timing of the pulsed light $Ld_6$. However, the exposure period of the frame (N-1) includes a part of period of the pulsed light $Ld_4$ and the entire illumination periods of the pulsed light $Ld_5$ and $Ld_7$ in addition to the illumination period $T_{Ld6}$ of the pulsed light $Ld_6$. Therefore, in the same manner as in the case of the non-overlap line in the second embodiment, the image processing unit 45 calculates the illumination time pixel signal by using the formula (8) which takes into account a ratio between the illumination period of the pulsed light $Ld_6$ and the illumination period of other pulsed light $Ld_4$, $Ld_5$, and $Ld_7$.

$$(\text{Pixel } x \text{ of } V\text{-}th \text{ line exposed with pulsed light } Ld_6) = \tag{8}$$
$$(\text{Pixel } x \text{ of } V\text{-}th \text{ line of }$$
$$D_{(N-1)}(\text{exposed with pulsed light } Ld_4 \text{ to } Ld_7)) \times$$
$$\frac{\text{Exposure period by pulsed light } Ld_6 \text{ of } D_{(N-1)}}{\text{Total exposure period by pulsed light } Ld_4 \text{ to } Ld_7 \text{ of } D_{(N-1)}} =$$
$$(\text{Pixel } x \text{ of } V\text{-}th \text{ line of }$$
$$D_{(N-1)}(\text{exposed with pulsed light } Ld_4 \text{ to } Ld_7)) \times \frac{1}{3.5}$$

Then, reference will be made to a case in which an illumination time pixel signal is generated for the pulsed light $Ld_4$ in (1) of FIG. 13. The illumination period $T_{Ld4}$ of the pulsed light $Ld_4$ overlaps with the read timing $R_{(N-2)}$ in the frame (N-2). In this case, for any horizontal line V, the illumination time pixel signal is generated based on the pixel signal of the horizontal line V in the pixel signal $D_{(N-2)}$ of the frame (N-2) read at an overlap timing overlapping with the illumination timing of the pulsed light $Ld_4$ and the pixel signal of the horizontal line V in the pixel signal $D_{(N-1)}$ of the frame (N-1) immediately after the overlap timing. However, the exposure period of the frame (N-2) includes the illumination periods of the pulsed light $Ld_1$ to $Ld_3$ in addition to the first half of the illumination period $T_{Ld4}$ of the pulsed light $Ld_4$. Further, the exposure period of the frame (N-1) includes the illumination periods of the pulsed light $Ld_5$ to $Ld_7$ in addition to the second half of the illumination period $T_{Ld4}$ of the pulsed light $Ld_4$. Therefore, the image processing unit 45 performs calculation for the frame (N-2) and the frame (N-1) respectively in view of ratios between the illumination period of the pulsed light $Ld_4$ and the illumination periods of the other pulsed light for each pixel x of any horizontal line V, and synthesizes the calculation results. Specifically, the illumination time pixel signal of each pixel x of the horizontal line V, which is an overlap line, is calculated by using the formula (9).

$$(\text{Pixel } x \text{ of } V\text{-}th \text{ line exposed with pulsed light } Ld_4) = \tag{9}$$
$$(\text{Pixel } x \text{ of } V\text{-}th \text{ line of }$$
$$D_{(N-2)}(\text{exposed with pulsed light } Ld_1 \text{ to } Ld_4)) \times$$
$$\frac{\text{Exposure period by pulsed light } Ld_4 \text{ of } D_{(N-2)}}{\text{Total exposure period by pulsed light } Ld_1 \text{ to } Ld_4 \text{ of } D_{(N-2)}} +$$
$$(\text{Pixel } x \text{ of } V\text{-}th \text{ line of }$$
$$D_{(N-1)}(\text{exposed with pulsed light } Ld_4 \text{ to } Ld_7)) \times$$
$$\frac{\text{Exposure period by pulsed light } Ld_4 \text{ of } D_{(N-1)}}{\text{Total exposure period by pulsed light } Ld_4 \text{ to } Ld_7 \text{ of } D_{(N-2)}} =$$

-continued (Pixel $x$ of V-th line of $D_{(N-2)}$(exposed with pulsed light $Ld_1$ to $Ld_4$))$\times \dfrac{0.5}{3.5}$ + (Pixel $x$ of V-th line of $D_{(N-1)}$(exposed with pulsed light $Ld_4$ to $Ld_7$))$\times \dfrac{0.5}{3.5}$ In the case of the rolling shutter method, the fractional terms (exposure time ratio) of the arithmetic expression vary for each horizontal line. However, in the case of the global shutter method, the fractional terms of the arithmetic expression are fixed values. When a CCD image sensor is employed in the imaging unit 24, in the same manner as in the first and second embodiments, the display controller 47 generates the display image signal based on the illumination time pixel signal generated by the image processing unit 45.

Third Embodiment

Next, a third embodiment will be described. In the third embodiment, a case will be described in which a PWM method is employed where an output width (illumination period) of pulsed light is variable.

Figure 14:
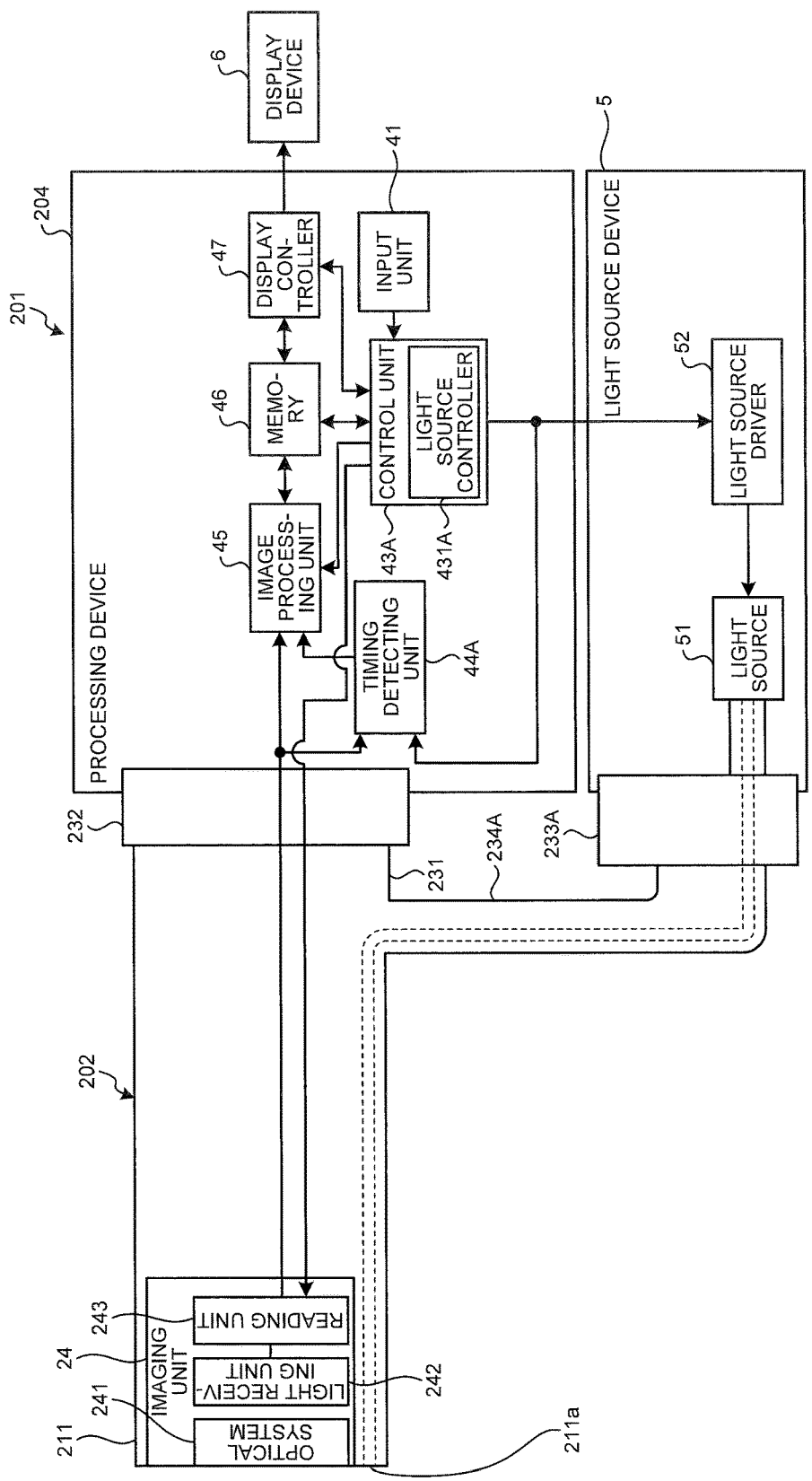
FIG. 14 is a block diagram schematically illustrating a configuration of an endoscope system according to a third embodiment.

FIG. 14 is a block diagram schematically illustrating a configuration of an endoscope system 201 according to the third embodiment. As illustrated in FIG. 14, the endoscope system 201 includes a processing device 204 instead of the processing device 4 illustrated in FIG. 2. The endoscope system 201 does not have the voice input device 3, the cord 31, and the connector 311 illustrated in FIG. 2. A connector 233A of a branch cord 234A of a universal cord of an endoscope 202 is configured to be connected to the light source device 5, and does not have the splitter 53 and the light detector 54 illustrated in FIG. 2.

A control unit 43A of the processing device 204 includes a light source controller 431A that controls the pulse width (illumination period) of the pulsed light output from the light source 51 based on the brightness of the pixel signal read by the imaging unit 24. The light source controller 431A performs control in which the illumination timing of the pulsed light of the light source 51 is synchronized with the frame cycle of the imaging unit 24. A timing detecting unit 44A detects a line where the illumination timing and the illumination period in which the illumination time pixel signal is generated and the read timing overlap with each other from among the pixel signals read from the imaging unit 24 based on a light source control signal of the light source controller 431A and the vertical synchronizing signal and the horizontal synchronizing signal attached to the pixel signal output from the imaging unit 24.

Figure 15:
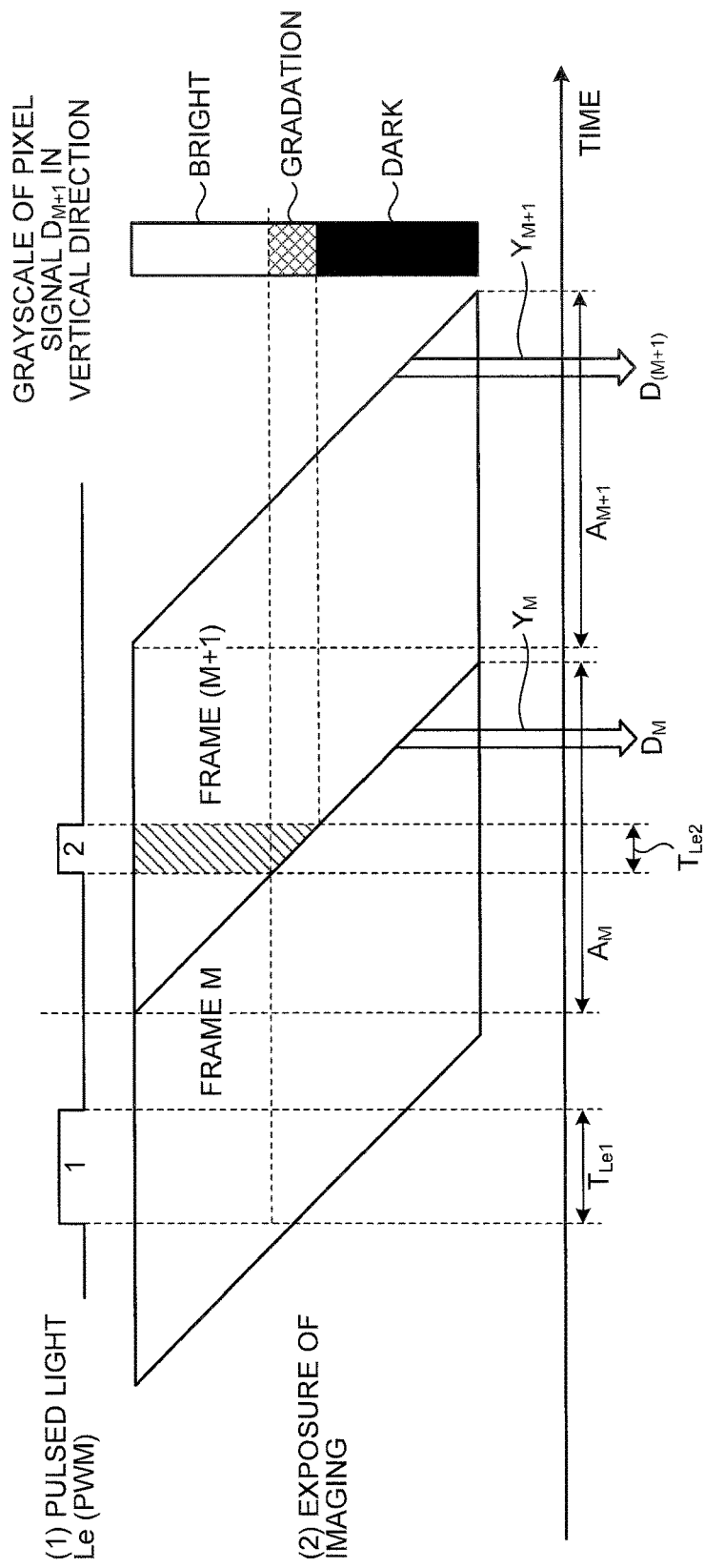
FIG. 15 is a diagram for explaining an illumination timing of pulsed light by a light source and exposure and read timings by a reading unit illustrated in FIG. 14.

(1) of FIG. 15 is a diagram illustrating an example of a timing chart illustrating the illumination timing of pulsed light Le emitted from the light source 51. (2) of FIG. 15 is a diagram illustrating an example of a timing chart for explaining the exposure timing and the read timing of the reading unit 243 of the imaging unit 24. In the example of FIG. 15, the illumination cycle of the pulsed light of the light source 51 and the frame cycle of the imaging unit 24 are the same cycle. The pulse width (illumination period) of the pulsed light from the light source 51 is different between the pulsed light $Le_1$ emitted in the exposure period of the frame M and the pulsed light $Le_2$ emitted to the frame (M+1). In the example of FIG. 15, the illumination period $T_{Le1}$ of the pulsed light $Le_1$ is longer than the illumination period $T_{Le2}$ of the pulsed light $Le_2$. Each horizontal line is sequentially exposed and the pixel signal is read in order from the first horizontal line in a period $A_M$, so that the pixel signal $D_M$ of the frame M is generated as illustrated by an arrow YM. Each horizontal line is sequentially exposed and the pixel signal is read in order from the first horizontal line in a period $A_{M+1}$, so that the pixel signal $D_{(M+1)}$ of the frame (M +1) is generated as illustrated by an arrow $Y_{M+1}$. As illustrated in the right area of FIG. 15, the grayscale of the pixel signal $D_{(M+1)}$ of the frame (M+1) in the vertical direction is bright in the upper area which is exposed with the pulsed light $Le_2$, gradually becomes dark (gradation) in an area where the illumination period $T_{Le2}$ of the pulsed light $Le_2$ and the read timing of the frame (M+1) overlap with each other, and becomes dark in the lower area where the pixel signals corresponding to the exposure by the pulsed light $Le_2$ had been read in the frame M.

Therefore, in the processing device 204, to generate the illumination time pixel signal corresponding to each pulsed light having a different pulse width, first, in the same manner as in the first and second embodiments, the timing detecting unit 44A detects the illumination timing and the illumination period of the pulsed light from the light source 51 and the read timing of each horizontal line of the light receiving unit 242 by the reading unit 243. The timing detecting unit 44A detects a horizontal line, where the read timing overlaps with the illumination period in which the illumination time pixel signal is generated, as an overlap line from among the pixel signals read from the reading unit 243.

Figure 16A:
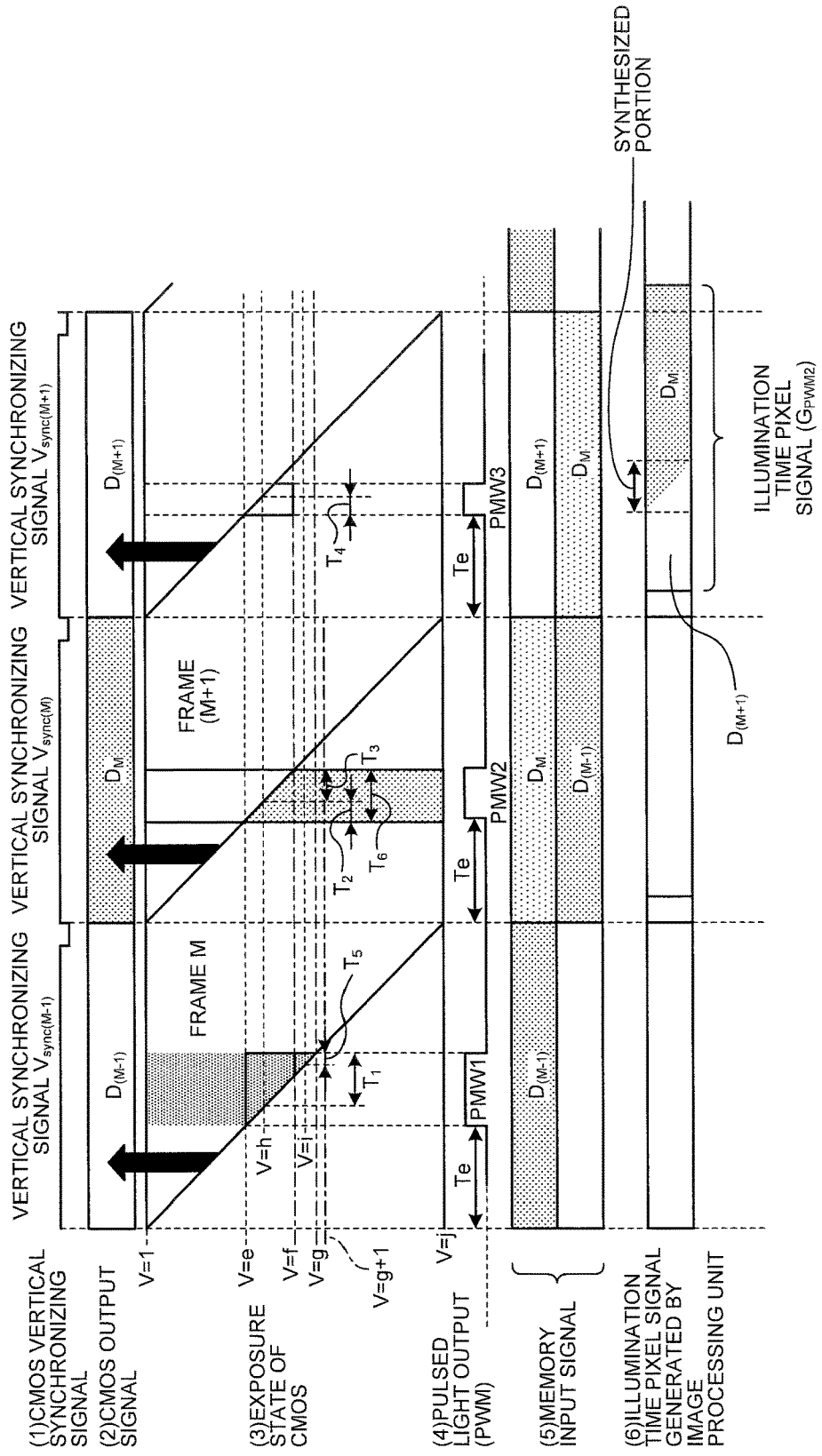
FIG. 16A is a timing chart illustrating a processing state of an imaging unit and each element of a processing device according to the third embodiment.
Figure 16B:
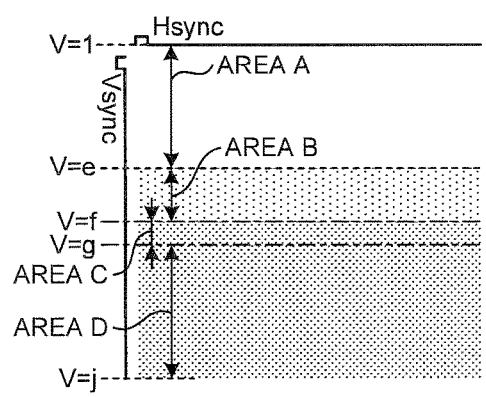
FIG. 16B is a schematic diagram for explaining an image of an illumination time pixel signal corresponding to pulsed light generated by an image processing unit in the third embodiment.

Next, the generation processing of the illumination time pixel signal by the image processing unit 45 will be described. FIG. 16A is a timing chart illustrating a processing state of the imaging unit 24 and each element of the processing device 204 according to the third embodiment. (1) of FIG. 16A is a timing chart illustrating an output of the vertical synchronizing signal in the CMOS image sensor constituting the imaging unit 24. (2) of FIG. 16A is a timing chart illustrating a data output from the reading unit 243 of the CMOS image sensor. (3) of FIG. 16A is a timing chart illustrating an exposure state of the CMOS image sensor. (4) of FIG. 16A is an exemplary timing chart illustrating the illumination timing of the pulsed light (PWM) emitted from the light source 51. (5) of FIG. 16A is a timing chart illustrating a pixel signal of each frame input into the memory 46. (6) of FIG. 16A is a timing chart illustrating the illumination time pixel signal generated by the image processing unit 45. FIG. 16B is a schematic diagram for explaining an image of an illumination time pixel signal ($G_{PWM2}$) corresponding to pulsed light (PWM2) generated by the image processing unit 45. The pulse signal of each pulsed light (PWM1, PWM2) rises in a period Te after the rise of the corresponding vertical synchronizing signal.

As an example, reference will be made to a case in which the image processing unit 45 generates the illumination time pixel signal ($G_{PWM2}$) corresponding to a pixel signal generated when all the pixels of the light receiving unit 242 are exposed with the pulsed light (PWM2) in (4) of FIG. 16A. In FIG. 16A, the non-overlap lines are the horizontal line 1 to the horizontal line e and the horizontal line (f+1) to the last horizontal line j among the horizontal lines V (V is an integer. V=1, . . . , e, . . . , h . . . , f, . . . , i, . . . , g, . . . , j). The overlap lines are the horizontal line (e+1) to the horizontal line f.

First, the generation of the illumination time pixel signal for the horizontal lines 1 to e among the non-overlap lines will be described. For the horizontal lines 1 to e, the entire illumination period $T_6$ of the pulsed light PWM2, in which the illumination time pixel signal is generated, is included in the exposure period of the horizontal lines 1 to e of the frame (M+1). For the horizontal lines 1 to e, the other pulsed is not emitted in the exposure period of the frame (M+1). Therefore, the image processing unit 45 directly outputs data of each pixel of the horizontal lines 1 to e of the pixel signal $D_{(M+1)}$ of the frame (M+1) that is read at the read timing immediately after the illumination timing of the pulsed light PWM2 as the illumination time pixel signal of the pulsed light PWM2 of the horizontal lines 1 to e (see area A in FIG. 16B). Also for the horizontal lines (g+1) to j, the entire illumination period $T_6$ of the pulsed light (PWM2) is included in the exposure period of the horizontal lines (g+1) to j of the frame M and the other pulsed light is not emitted in the exposure period of the frame M. Therefore, the image processing unit 45 directly outputs data of each pixel of the horizontal lines (g+1) to j of the pixel signal $D_M$ of the frame M that is read at the read timing immediately after the illumination timing of the pulsed light PWM2 as the illumination time pixel signal of the pulsed light PWM2 of the horizontal lines (g+1) to j (see area D in FIG. 16B).

Next, the generation of the illumination time pixel signal for the horizontal line i (f+1≤i≤g) among the non-overlap lines will be described. For the horizontal line i, in addition to the illumination period $T_6$ of the pulsed light PWM2 in which the illumination time pixel signal is generated, the illumination period $T_5$ of a part of the pulsed light PWM1 that is emitted before the pulsed light PWM2 is included in the exposure period of the horizontal line i of the frame M. For each pixel x of the horizontal line i, the image processing unit 45 calculates the illumination time pixel signal by using the formula (10) which takes into account a ratio between the illumination period $T_6$ of the pulsed light PWM2 and the illumination period $T_5$ of a part of the pulsed light (PWM1) that is emitted before the pulsed light PWM2 for the pixel signal of the horizontal line i of the pixel signal $D_M$ of the frame M that is read at the read timing immediately after the illumination timing of the pulsed light PWM2. In other words, the area C in FIG. 16B corresponding to the horizontal line i (f+1≤i≤g) is formed by a signal obtained by applying a gain correction to the pixel signal $D_M$.

$$(\text{Pixel } x \text{ of } i\text{-}th \text{ line exposed with pulsed light } PWM2) = \quad (10)$$
$$(\text{Pixel } x \text{ of } i\text{-}th \text{ line of } D_M) \times \frac{T_6}{T_5 + T_6}$$

Next, the generation of the illumination time pixel signal for the horizontal line h (e+1≤h≤f) which is an overlap line will be described. For the horizontal line h, the image processing unit 45 generates the illumination time pixel signal based on the pixel signal of the horizontal line h in the pixel signal $D_M$ of the frame M read at an overlap timing overlapping with the illumination timing of the pulsed light PWM2 and the pixel signal of the horizontal line h in the pixel signal $D_{(M+1)}$ of the frame (M+1) immediately after the overlap timing. However, the exposure period of the horizontal line h of the frame M includes the second half period $T_1$ of the illumination period of the pulsed light (PWM1) emitted before the pulsed light (PWM2) in addition to the first half period $T_2$ of the illumination period $T_6$ of the pulsed light (PWM2). Further, the exposure period of the horizontal line h of the frame (M+1) includes the first half period $T_4$ of the illumination period of the pulsed light PWM3 emitted after the pulsed light PWM2 in addition to the second half period $T_3$ of the illumination period $T_6$ of the pulsed light PWM2.

Therefore, the image processing unit 45 calculates the pixel signal of the horizontal line h in receiving only the pulsed light PWM2 in the frame M in view of a ratio between the first half period $T_2$ of the illumination period of the pulsed light PWM2 and the second half period $T_1$ of the illumination period of the pulsed light PWM1 before the pulsed light PWM2 for each pixel x of the horizontal line h. Then, the image processing unit 45 calculates the pixel signal of the horizontal line h in receiving only the pulsed light PWM2 in the frame (M+1) in view of a ratio between the second half period $T_3$ of the illumination period of the pulsed light PWM2 and the first half period $T_4$ of the illumination period of the pulsed light PWM3 following the pulsed light PWM2. The image processing unit 45 calculates the illumination time pixel signal of each pixel x of the horizontal line h by synthesizing the pixel signal of the horizontal line h in receiving only the pulsed light PWM2 in the frame M and the pixel signal of the horizontal line h in receiving only the pulsed light PWM2 in the frame (M+1). Specifically, the illumination time pixel signal of each pixel x of the horizontal line h, which is an overlap line, is calculated by using the formula (11). Therefore, the area B in FIG. 16B corresponding to the horizontal line h (e+1≤h≤f) is formed by a synthesized signal of the pixel signal $D_M$ and pixel signal $D_{(M+1)}$.

$$(\text{Pixel } x \text{ of } h\text{-}th \text{ line exposed with pulsed light } PWM2) = \quad (11)$$
$$(\text{Pixel } x \text{ of } h\text{-}th \text{ line of } D_M) \times \frac{T_2}{T_1 + T_2} +$$
$$(\text{Pixel } x \text{ of } h\text{-}th \text{ line of } D_{M+1}) \times \frac{T_3}{T_3 + T_4}$$

When the illumination period of the pulsed light emitted from the light source is made variable by using the PWM method as in the third embodiment, the illumination time pixel signal may be calculated by considering whether each pixel is located in an overlap line or a non-overlap line and a ratio between an illumination period of pulsed light in which the illumination time pixel signal is generated and an illumination period of the other pulsed light included in the exposure period of the line. Also in the third embodiment, the display controller 47 may generate the display image signal based on the illumination time pixel signal generated by the image processing unit 45 in the same manner as in the first and second embodiments.

The reading unit 243 only has to be able to perform exposure control and read control of the light receiving unit 242, so that the reading unit 243 does not necessarily have to be provided in the imaging unit 24 and the reading unit 243 may be provided in the previous stage of the image processing unit 45 of the processing device 4 or 204.

In the embodiment, the splitter 53 only has to be provided on a light path of the pulsed light emitted from the light source 51, and the light detector 54 only has to be provided at a position where the light split by the splitter 53 is received. For example, as illustrated in FIG. 17, the splitter 53 and the light detector 54 may be provided in an adapter 7 for connecting to the connector 233A of a universal cord 23A and to a connector 55 of the light source device 5.

Figure 17:
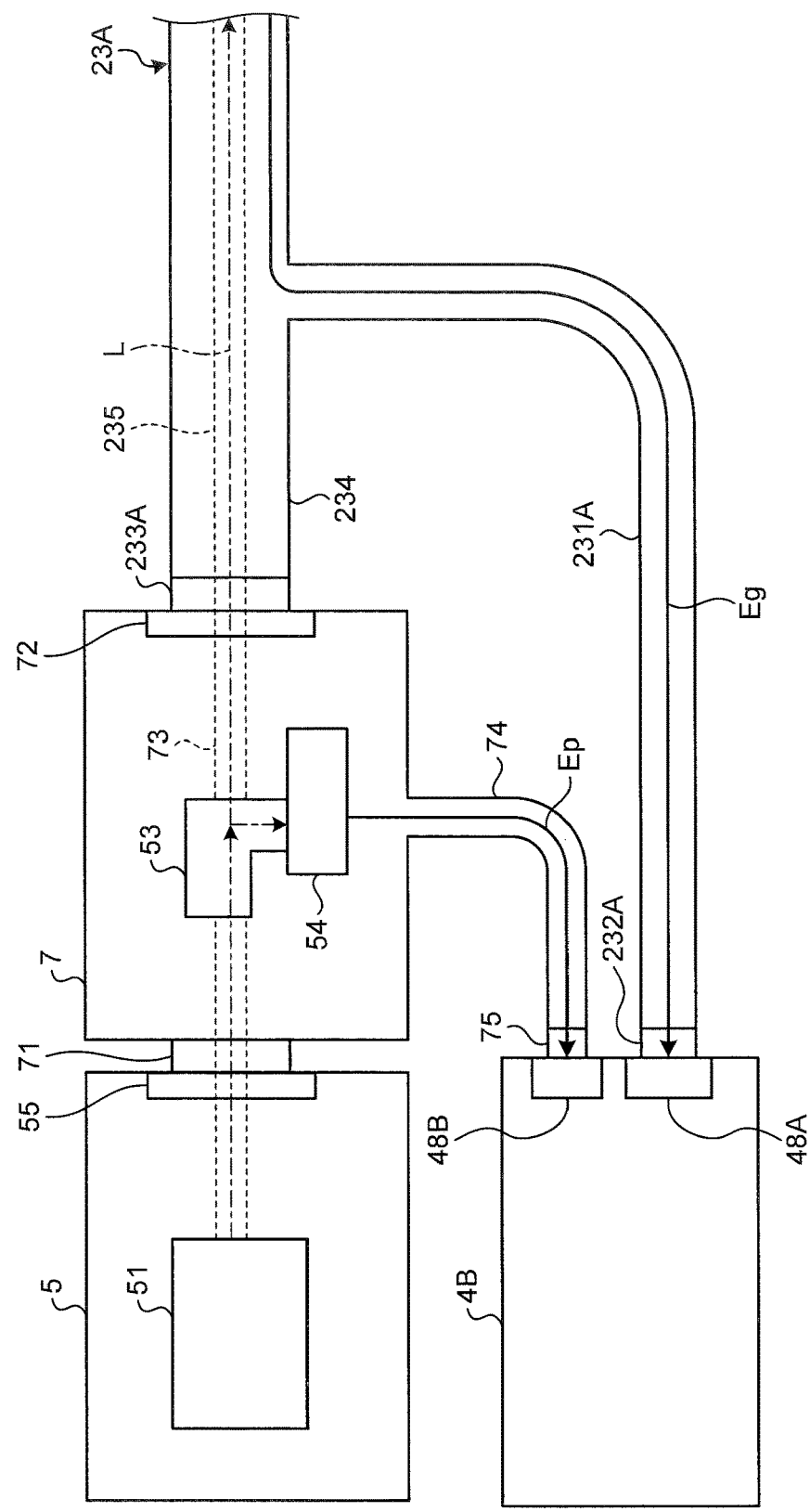
FIG. 17 is a schematic diagram illustrating a case in which a splitter and a light detector are provided in an adaptor.

As illustrated in FIG. 17, the adapter 7 includes a connector 71, a connector 72, a light guide cable 73, the splitter 53 provided on a propagation path of pulsed light L of the light guide cable 73, the light detector 54, a pulse signal cord 74, and a connector 75. The connector 71 is connected to the connector 55 of the light source device 5. The connector 72 is connected to the connector 233A of the universal cord 23A. The light guide cable 73 propagates the pulsed light L of the light source 51 to a light guide cable 235 of the universal cord 23A. The pulse signal cord 74 transmits a pulse signal Ep converted by the light detector 54 to a processing device 4B. The connector 75 is provided at an end portion of the pulse signal cord 74 and is connected to a connector 48B of the processing device 4B. In the processing device 4B in FIG. 17, a connector 48A is also illustrated. The connector 48A is connected with a connector 232A at an end portion of a branch cord 231A having a transmission cable of an image signal Eg.

Figure 18:
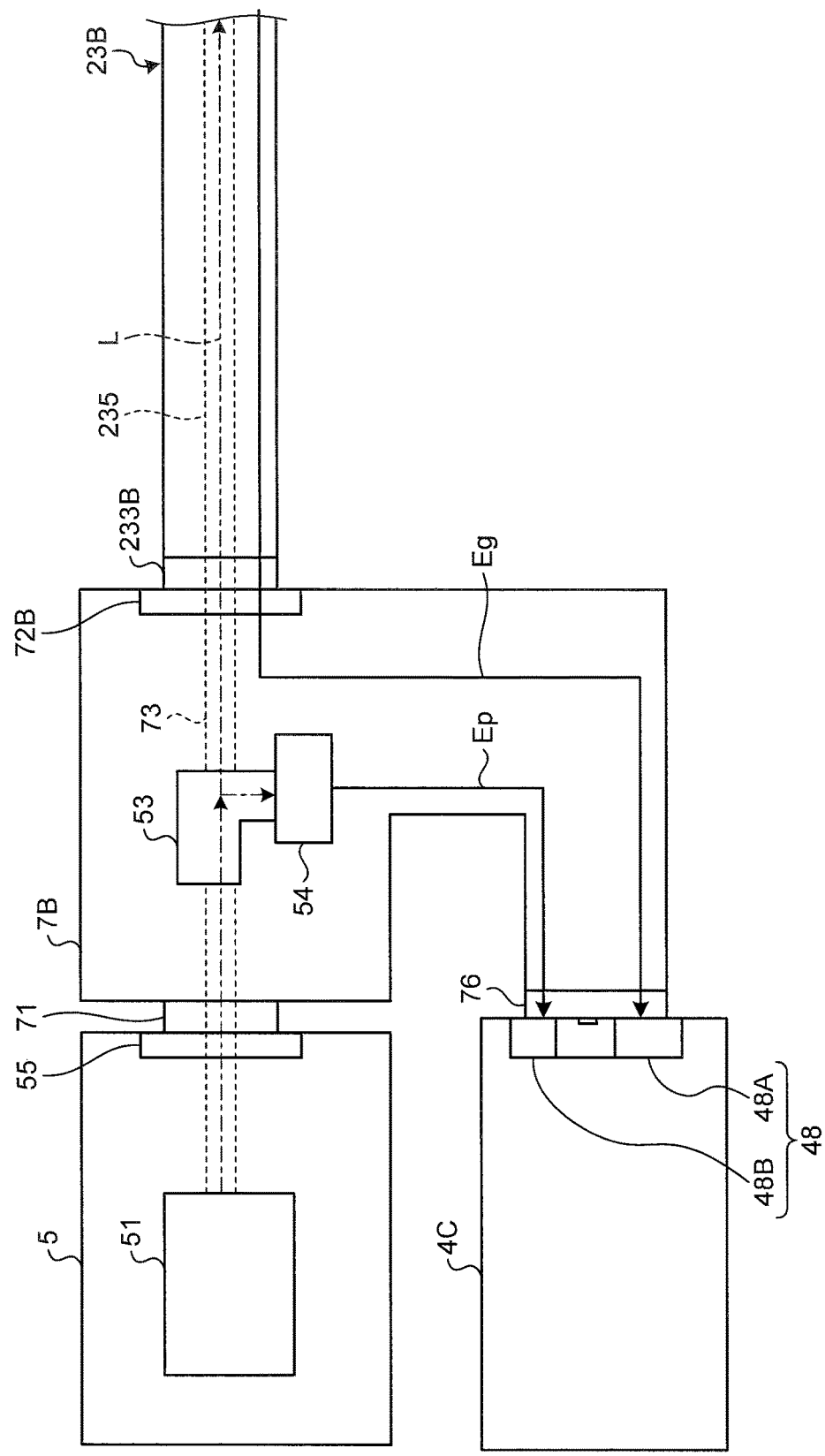
FIG. 18 is a block diagram schematically illustrating another case in which a splitter and a light detector are provided in an adaptor.

In FIG. 18, a processing device 4C, the light source device 5, and an integrated connector 233B at an end portion of a universal cord 23B are connected by an integrated adapter 7B. In this configuration, the splitter 53 and the light detector 54 may be provided in the integrated adapter 7B. A main body of the integrated adapter 7B includes the connector 71 for connecting to the connector 55 of the light source device 5, an integrated connector 76 for connecting to an integrated connector 48 of the processing device 4C, and an integrated connector 72B for connecting to the integrated connector 233B at an end portion of the universal cord 23B, in addition to the splitter 53 and the light detector 54. When the pulsed light is emitted from the light source device 5, the adapter 7 or 7B illustrated in FIG. 17 or FIG. 18 is employed. When light other than the pulsed light is emitted from the light source device 5, an adapter which does not have the splitter 53 and the light detector 54 is employed, which makes it possible to prevent attenuation of the amount of light due to passing through the splitter 53 when the light other than the pulsed light is emitted. The processing devices 4B and 4C illustrated in FIG. 17 and FIG. 18 have the same configuration as that of the processing device 4. However, as for the light source device 5, FIG. 17 and FIG. 18 illustrate only main elements.

An execution program for each process executed in the image processing unit 45 and the other elements according to the embodiments may be provided by being recorded in a computer-readable recording medium such as a CD-ROM, a flexible disk, a CD-R, and a DVD (Digital Versatile Disk) as a file in an installable format or an executable format or may be provided by being stored on a computer connected to a network such as the Internet and being downloaded through the network. Further, the execution program may be provided or distributed through a network such as the Internet.

According to some embodiments, an illumination time pixel signal is generated from a pixel signal of a plurality of pixels that has received light from a subject irradiated with pulsed light, according to an overlapping state between illumination timing of the pulsed light and read timing of the pixel signal. The illumination time pixel signal is a pixel signal generated when the plurality of pixels is exposed in an illumination period of the pulsed light. With this feature, it is possible to maintain image quality even if the pulsed light is emitted at any timing with respect to the read timing of an image sensor.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A processing device comprising:
an input terminal configured to input a pixel signal from an image sensor including plural horizontal lines each having plural pixels, wherein the image sensor receives light from a subject illuminated by pulsed light generated by alternating an illumination period of illuminating the subject and a non-illumination period of not illuminating the subject, and output the pixel signal; and
a processor comprising hardware, the processor configured to:
input the pixel signal through the input terminal;
synthesize, with regard to a first horizontal line in which a first read-out timing falls within the illumination period of the pulsed light, among the plural horizontal lines, a first pixel signal read from the first horizontal line at the first read-out timing and a second pixel signal read from the first horizontal line at a second read-out timing that is immediately after the first read-out timing, thereby to generate a third pixel signal; and
allow the illumination period to start and end in a reading period during which the pixel signals are read sequentially from a foremost horizontal line through a last horizontal line among the plural horizontal lines, wherein the illumination period is shorter than the reading period.

2. The processing device according to claim 1, wherein the processor is further configured to read, with regard to a second horizontal line in which the first read-out timing comes before the illumination period of the pulsed light, a fourth pixel signal from the second horizontal line at the second read-out timing.

3. The processing device according to claim 2, wherein the processor is further configured to read, with regard to a third horizontal line in which the first read-out timing comes after the illumination period of the pulsed light, a fifth pixel signal from the first horizontal line at the first read-out timing.

4. The processing device according to claim 3, wherein the processor is further configured to synthesize the third pixel signal, the fourth pixel signal, and the fifth pixel signal, thereby to generate an image signal corresponding to one frame.

5. The processing device according to claim 2, wherein the processor is further configured to detect the illumination period of the pulsed light and the first read-out timing, thereby to discriminate the first horizontal line and the second horizontal line from the plural horizontal lines.

6. An imaging device comprising:
an image sensor including:
plural pixels provided in each of plural horizontal lines, so as to receive light from a subject illuminated by pulsed light generated by alternating an illumination period of illuminating the subject and a non-illuminating period of not illuminating the subject, thereby to generate a pixel signal; and
a reading circuit that controls exposure to the plural pixels and reading of the pixel signal from the plural pixels, and
a processor comprising hardware, the processor configured to:
input the pixel signal from the image sensor; and
synthesize, with regard to a first horizontal line in which a first read-out timing falls within the illumination period of the pulsed light, among the plural horizontal lines, a first pixel signal read from the first horizontal line at the first read-out timing and a second pixel signal read from the first horizontal line at a second read-out timing that is immediately after the first read-out timing, thereby to generate a third pixel signal; and allow the illumination period to start and end in a reading period during which the pixel signals are read sequentially from a foremost horizontal line through a last horizontal line among the plural horizontal lines, wherein the illumination period is shorter than the reading period.

7. The imaging device according to claim 6, wherein the processor is further configured to read, with regard to a second horizontal line in which the first read-out timing comes before the illumination period of the pulsed light, a fourth pixel signal from the second horizontal line at the second read-out timing.

8. The imaging device according to claim 7, wherein the processor is further configured to read, with regard to a third horizontal line in which the first read-out timing comes after the illumination period of the pulsed light, a fifth pixel signal from the first horizontal line at the first read-out timing.

9. The imaging device according to claim 8, wherein the processor is further configured to synthesize the third pixel signal, the fourth pixel signal, and the fifth pixel signal, thereby to generate an image signal corresponding to one frame.

10. The imaging device according to claim 7, wherein the processor is further configured to detect the illumination period of the pulsed light and the first read-out timing, thereby to discriminate the first horizontal line and the second horizontal line from the plural horizontal lines.

11. The imaging device according to claim 6, wherein the imaging sensor includes either one of a complementary metal-oxide semiconductor (CMOS) imaging element and a charge-coupled device (CCD) imaging element.

12. An endoscope system comprising:

a light source configured to emit pulsed light to illuminate a subject, wherein the pulsed light is generated by alternating an illumination period of illuminating the subject and a non-illuminating period of not illuminating the subject;

an image sensor including:
  plural pixels provided in each of plural horizontal lines, so as to receive light from the subject illuminated by the pulsed light, thereby to generate a pixel signal; and
  a reading circuit that controls exposure to the plural pixels and reading of the pixel signal from the plural pixels, and a processor comprising hardware, the processor configured to:
  input the pixel signal that have been read by the reading circuit; and
  synthesize, with regard to a first horizontal line in which a first read-out timing falls within the illumination period of the pulsed light, among the plural horizontal lines, a first pixel signal read from the first horizontal line at the first read-out timing and a second pixel signal read from the first horizontal line at a second read-out timing that is immediately after the first read-out timing, thereby to generate a third pixel signal; and
  control the light source to allow the illumination period to start and end in a reading period during which the pixel signals are read sequentially from a foremost horizontal line through a last horizontal line among the plural horizontal lines, wherein the illumination period is shorter than the reading period.

13. The endoscope system according to claim 12, wherein the processor is further configured to read, with regard to a second horizontal line in which the first read-out timing comes before the illumination period of the pulsed light, a fourth pixel signal from the second horizontal line at the second read-out timing.

14. The endoscope system according to claim 13, wherein the processor is further configured to read, with regard to a third horizontal line in which the first read-out timing comes after the illumination period of the pulsed light, a fifth pixel signal from the first horizontal line at the first read-out timing.

15. The endoscope system according to claim 14, wherein the processor is further configured to synthesize the third pixel signal, the fourth pixel signal, and the fifth pixel signal, thereby to generate an image signal corresponding to one frame.

16. The endoscope system according to claim 13, wherein the processor is further configured to detect the illumination period of the pulsed light and the first read-out timing, thereby to discriminate the first horizontal line and the second horizontal line from the plural horizontal lines.

17. The endoscope system according to claim 12, wherein the subject is a vocal cord.

18. The endoscope system according to claim 17, further comprising a voice input unit configured to input a voice, wherein the processor is further configured to:
  detect a vibration frequency of the voice input into the voice input unit; and
  control the light source such that a frequency of the pulsed light is in synchronization with the detected vibration frequency of the voice.

19. The endoscope system according to claim 12, wherein the processor is further configured to:
  instruct the light source to synchronize the illumination period with the reading period and to control the illumination period in accordance with the pixel signal read by the reading circuit.

* * * * *